United States Patent
Kokoszka et al.

(10) Patent No.: US 11,478,186 B2
(45) Date of Patent: Oct. 25, 2022

(54) CLUSTER-BASED SLEEP ANALYSIS

(71) Applicant: Fitbit, Inc., San Francisco, CA (US)

(72) Inventors: Alicia Yolanda Kokoszka, San Francisco, CA (US); Alexander Statan, Oakland, CA (US); Karla Theresa Gleichauf, San Francisco, CA (US)

(73) Assignee: FITBIT, INC., San Francisco, CA (US)

( * ) Notice: Subject to any disclaimer, the term of this patent is extended or adjusted under 35 U.S.C. 154(b) by 0 days.

(21) Appl. No.: 17/162,286

(22) Filed: Jan. 29, 2021

(65) Prior Publication Data

US 2022/0240843 A1 Aug. 4, 2022

(51) Int. Cl.
*A61B 5/00* (2006.01)
*G06K 9/62* (2022.01)

(52) U.S. Cl.
CPC .......... *A61B 5/4806* (2013.01); *A61B 5/0022* (2013.01); *A61B 5/6802* (2013.01); *A61B 5/744* (2013.01); *G06K 9/6218* (2013.01)

(58) Field of Classification Search
CPC ....... A61B 5/4806; A61B 5/68; A61B 5/6801; A61B 5/6802; G06K 9/6218
See application file for complete search history.

(56) References Cited

U.S. PATENT DOCUMENTS

| | | | | |
|---|---|---|---|---|
| 2016/0151603 | A1* | 6/2016 | Shouldice | H04R 3/00 600/28 |
| 2017/0352287 | A1* | 12/2017 | Arnold | G06F 3/04842 |
| 2019/0350535 | A1* | 11/2019 | Zhao | A61B 5/0022 |
| 2020/0077942 | A1 | 3/2020 | Youngblood et al. | |

FOREIGN PATENT DOCUMENTS

| | | |
|---|---|---|
| CN | 110448779 | 11/2019 |
| WO | WO 2020/002763 | 1/2020 |

OTHER PUBLICATIONS

Baker, Rosey, "The 4 Type of 'Sleep Animals' and How Knowing Yours Unlocks Your Potential", Jan. 9, 2017, https://www.elitedaily.com/wellness/types-sleep-animals-potential/1745946, 8 pages.

Casper Editorial Team, "How to Find Your Chronotype to Boost Productivity", Nov. 4, 2020, https://casper.com/blog/chronotype/, 18 pages.

(Continued)

*Primary Examiner* — Benyam Haile
(74) *Attorney, Agent, or Firm* — Dority & Manning, P.A.

(57) ABSTRACT

Various types of data can be collected regarding the physical or mental health of a user, as may relate to sleep of the user over a period of time. Health metrics can be determined from this data that can enable the user to be associated with a particular health type or category. For sleep, this can include associating the user with a sleep animal that has specific characteristics. This can help a user to better understand that user's sleep, and how that sleep compares to sleep of others. In addition to being able to provide health information in a way that is easy to understand, such an approach can also help to make more accurate recommendations or take specific actions to help improve the health of a user, such as to improve sleep. This can include making recommendations to a user or automatically adjusting operation of at least one device.

20 Claims, 8 Drawing Sheets

(56) References Cited

OTHER PUBLICATIONS

Rehman, Anis, "Chronotypes", Jan. 8, 2021, https://www.sleepfoundation.org/how-sleep-works/chronotypes, 10 pages.
International Search Report and Written Opinion for Application No. PCT/US2022/014235, dated Apr. 22, 2022, 17 pages.
Taillard et al., "Validation of Home and Ostberg Momingness-Eveningness Questionnaire in a Middle-Aged Population of French Workers", Journal of Biological Rhythms, vol. 19, No. 1, 2004, pp. 76-86.
Wahl et al., "Data and Expert Models for Sleep Timing and Chronotype Estimation from Smartphone Context Data and Simulations", Proceedings of the ACM on Interactive, Mobile, Wearable and Ubiquitous Technologies, vol. 2, No. 139, 2018, pp. 1-28.

* cited by examiner

CLUSTER-BASED SLEEP ANALYSIS

BACKGROUND

Various conventional approaches to sleep study and analysis involve individuals visiting a sleep clinic, where sleep of that individual may be monitored over the course of a single night. While such analysis can provide valuable information, it is difficult to determine an extent to which this sleep data is relevant to other nights or longer periods of time, as well as how an individual might sleep in their own bed in comfortable surroundings. Recent advances in wearable technology such as fitness trackers and smart watches have enabled the collection of sleep data at home, but the information surfaced to wearers of these devices is often overly generalized and does not provide the individual with an adequate understanding of their sleep, including whether there are areas for improvement or things that can be done to obtain that improvement that are relevant to that specific individual.

BRIEF DESCRIPTION OF THE DRAWINGS

Various embodiments in accordance with the present disclosure will be described with reference to the drawings, in which.

DETAILED DESCRIPTION

Figure 1:
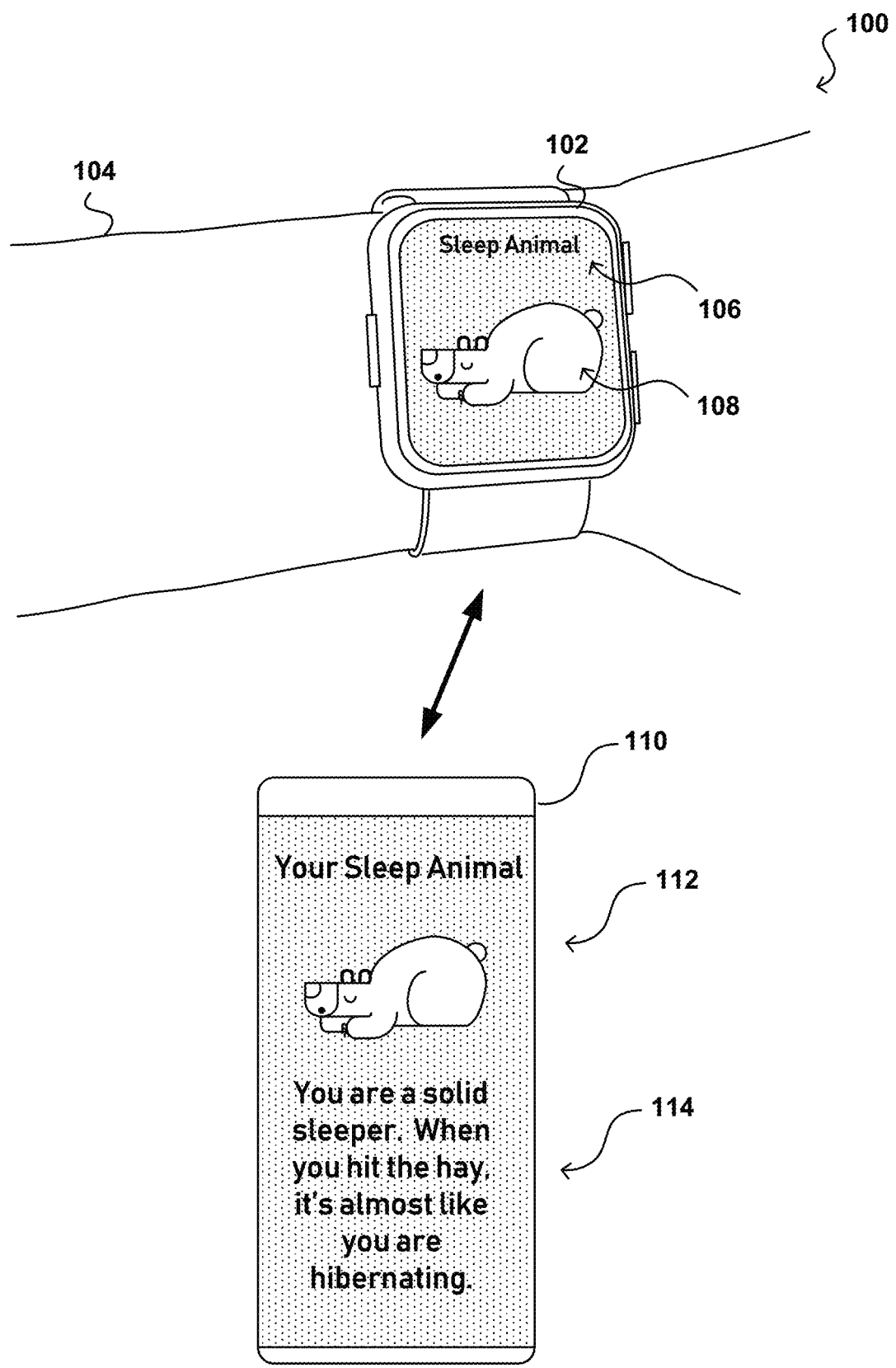
FIG. 1 illustrates example interface states that can be generated on different devices in accordance with various embodiments.

In the following description, various illustrative embodiments will be described. For purposes of explanation, specific configurations and details are set forth in order to provide a thorough understanding of the embodiments. However, it will also be apparent to one skilled in the art that the embodiments may be practiced without the specific details. Furthermore, well-known features may be omitted or simplified in order not to obscure the embodiments being described.

People are becoming ever-more health conscious, due in large part to the availability of digital health monitoring devices such as fitness trackers. Such devices are able to capture various types of information about a user, such as activity or motion data and resting heart rate, that can be used to infer information about a person wearing, or otherwise being associated with, one or more of those devices. At least some of these devices, or systems or services in communication with these devices, are able to analyze this and other data to provide information about the physical health of a person, as may include one or more sleep patterns of that person. This can include, for example, the time the person fell asleep and woke up, as well as periods of time during that sleep when the user may have been in different stages of sleep, such as deep sleep, light sleep, REM (rapid eye movement) sleep, awake, and so on. At least some of these devices may also provide a quantitative evaluation of the sleep of a person, such as to provide a sleep score that provides a measure of the quality of sleep that person obtained during a specific night or over a sequence of nights.

While this data may be at least somewhat useful for users, these users may often not fully understand the data or how to interpret the data. For example, a user might receive information indicating that they got 21 minutes of REM sleep one night, but they may not know whether that is too high, too low, or about right. Further, a user might receive a sleep score of 89 but not know what that represents, or what the target or average value should be. In some instances, these devices may offer recommendations that are based on this collected or inferred sleep data, such as to get more exercise, not drink alcohol or caffeine before bed, go to bed earlier, and so on. Unfortunately, such information can be relatively generic and may not be particularly helpful for any given individual. Further, if a person does not drink caffeine or alcohol, the person might not only think the recommendations are irrelevant, but may in fact be offended, which can reduce the overall value of the information and usefulness of the product or service.

Accordingly, approaches in accordance with various embodiments can provide for sleep analysis that is more detailed and relevant to specific individuals. Various approaches can also provide recommendations, visualizations, and discussion that are not only relevant to a particular individual, but that should be easy for most individuals to understand and follow. Various approaches can also automatically make or cause changes based on at least some of this sleep-related data, whether to a device being worn by a user or a device associated with an individual that can influence the sleep of that individual in some way.

FIG. 1 illustrates an example display approach 100 that can be utilized in accordance with at least one embodiment. In this example, a user can wear a wearable computer 102 or monitoring device, such as a fitness tracker or smart watch, on a wrist or arm 104 of that user. Other wearable computers or monitoring devices can be utilized as well that may be worn in other locations or ways, as may include smart rings, bands, earbuds, straps, clothing, contacts, patches, and other "smart" or network-connected devices. In many embodiments the wearable computer or device will include a touch sensitive display allowing the wearing user to input or receive information relevant to his or her physical or mental state as discussed herein. In this example, the wearable device can be in wireless communication (e.g., Bluetooth® or Wi-Fi) with at least one other computing device 110 associated with the user. Each of these devices 102, 110 can include some type of presentation mechanism, such as a display screen, that can be used to convey information to at least a user of the device. As known for such devices, a wearable device such as a fitness tracker may communicate with another user device, such as a smartphone, desktop computer, laptop, or table computer, as resources, battery life, and real estate may be limited on the wearable computer, such that it can be desirable to send data to another device for analysis and presentation, among other such options.

As will be discussed in more detail later herein, data for a user can be collected using a wearable device 102, associated computing device 110, or other electronic device or mechanism. The wearable device 102 may include various sensors, such as motion and temperature sensors, which can be used to measure or detect information about the user. The sensors in some illustrative embodiments are non-invasive and do not require that any sort of instrumentation be introduced into the wearing user's body. In one embodiment, a user interface can provide the capability for the user to enter designated data. The wearable device 102 can also include an optical measurement sub-system including at least one optical emitter and at least one optical detector or receiver. The emitter can emit light of one or more wavelengths that can be reflected from the surface of the user's skin, or diffusely reflected after traveling under the surface, and detected by at least one of the receivers. Such an optical assembly can enable the monitoring device 102 to measure various types of information during times in which the user is wearing the monitoring device.

At least some of this collected data can be analyzed to attempt to determine a type or category of "sleeper" to which the user corresponds. It can be valuable to a user to be able to determine a type of sleeper, or sleeper type, as the user may then be able to better understand their sleep relative to other sleepers of that sleeper type. Further, recommendations can be provided that are more relevant to a type of sleeper, and thus more likely to be relevant to a particular user of that type. Further still, such categorization can help to provide analysis that is relatively specific to that user, but that can be provided or visualized in a way that should be relatively easy for most users to understand, particularly with respect to sleep of similar users.

In at least one embodiment, sleep-related data collected for a user can be analyzed and used to determine a category or type of sleeper to which that user belongs. In at least one embodiment, data for multiple users can be analyzed and used generate a set of sleeper types or categories into which users might fall. Once these categories or sleeper types are determined, such as discussed in more detail elsewhere herein, the relevant aspects of each type can be determined and contrasted against those of other types, in order to determine the most distinguishing habits (or patterns or features, etc.) of each sleeper type. In at least one embodiment, these habits can then be analyzed to attempt to associate a category label that is representative of that respective sleeper type, which should be easy for a user to understand.

An example of a sleeper type label can be a "sleep animal." Each sleep animal can be representative of a respective sleeper type, and may be at least somewhat indicative of that sleeper type in a way that is understandable to a user. For example, a "bear" sleep animal might be associated with a sleeper type where a person tends to get long periods of deep sleep, similar to a bear hibernating. Another example might be a "kangaroo" sleep animal where a user frequently "hops" between different sleep states, or a "hummingbird" sleep animal where a user gets much more light sleep than most. Various other labels, types, can characteristics can be used as well within the scope of the various embodiments. Such an approach can provide a relatively simple and easy way for a user to understand the type of sleeper they are, at least relative to other sleepers, and in particular to other similar sleepers. Further, if a user switches between sleeper types over time then this provides a relatively simple way for the user to understand the change and follow those changes over time. In some embodiments, sleep animals may be associated with different health outcomes, particularly certain profiles of body mass index (BMI), resting heart rate (RHR), and heart rate variability (HRV).

An advantage to such an approach to labeling is that visualizations can be provided that may be easier for various types of users to understand and follow. For example, a relatively simple animated version of a sleep animal 108 can be presented on a display of a wearable computer, along with other relevant information 106. This can be presented at various times to remind the user of the type of sleeper they are, which may help them to make decisions on activities based at least in part upon characteristics of that sleeper type. Further, this sleep animal can be presented at specific times where it is desired to prompt the user or convey specific information, such as when a user should consider going to sleep, winding down, etc. In at least some embodiments, the sleep animal can be animated to convey this or other such information, such as the sleep animal turning off a light or device, getting in bed, setting an alarm, and so on. In at least some embodiments, the presentation of a sleep animal on a wearable computer may also convey that additional information is available on a related device, such as a connected smartphone, that may provide more detailed information. For example, a brief summary may be provided on the wearable computer and the user can access the connected user device 110 to obtain additional detail or content 114. A user may also be able to access additional information on other devices as well, such as through a browser on a desktop or laptop computer with access through a user account.

In one example, six archetypal sleeper types were defined and developed that exist across an identified population. In this example, there were also eleven sleep metrics selected or defined from the available metrics or data, which can be used to assess how a user slept over a period of time, such as the past 28 nights, in comparison to others like them, such as of the same or similar sleeper type. It should be understood, however, that there can be additional, fewer, or alternative types or metrics in different embodiments or implementations, where the number of types utilized can depend upon factors such as the type and results of clustering, types of health metric(s) being monitored, population evaluated, and so on. A user profile, such as a sleep bio, can then be generated based at least in part upon a respective sleeper type and values for these advanced sleep metrics, which can help to educate a user about their sleeper type using their sleep animal, as well as how that user rates across those advanced sleep metrics. These bios can be static, based on determined information for a user or a sleeper type, or can be a dynamic and update as new sleep-related data, recommendations, or other information is obtained, received, updated, or generated.

In at least one embodiment, the ability to utilize historical sleep data for a user enables selection of a personalized characterization of their sleep behavior in the form of, for example, a sleep animal or other characterization that provides an easy to understand but personalized assessment of their sleep. Other examples of characterizations can include types of people, geography, weather, vehicles, and the like, where different aspects of those characterizations can be associated with different aspects of the sleep of various users. Further, as mentioned herein such an approach is not limited to sleep but can be used for other physical or mental health aspects as well, as may relate to mental state, physical health, fitness, personality type, and the like. A bio, or other interface or presentation of content, can be used to provide visualizations educating a user on how they sleep in comparison to others like them across the advanced sleep metrics. Characterization of a user's typical sleep can identify opportunities for the user to improve that user's sleep and make the user feel like the health monitoring system, service, or device truly understands that user.

In various embodiments, a sleep bio can complement other sleep related information, such as a sleep score that evaluates the quality of sleep from the prior night. In particular, a given sleep score may rate, or be calculated from, factors such as the time asleep and awake, time in deep and REM (rapid eye movement) sleep, and sleeping heart rate and restlessness for the past night. As mentioned, however, such a score on its own can lack any analysis of longitudinal sleeping patterns such as sleep consistency, sleep chronotype, sleep fragmentation possibly from insomnia or apnea, and multiphasic sleeping patterns. A sleep bio can help to characterize and visualize a user's sleep from a period such as the past 28 nights, which can be used as the foundation for developing a sleep report card, or other such presentation of content, that assesses a user's sleep over, for example, the past month. In at least one embodiment, such sleep profiles can help quantify "good" or "bad" sleep, or "better" or "worse" sleep relative to one or more prior periods or other users, etc., and can use this information to create an actionable sleep report card, which may also support a larger range or presentation of health-related actionable summary scores. Collecting data over several nights or sleep periods can also help to determine probabilities of sleep for a user, which can also help to make better recommendations for a user based not only on past sleep, but also anticipated sleep.

In order to determine a sleeper type for a user, a determination is first made in at least some embodiments as to the possible sleeper types. This can include collection and analysis of data for multiple users, then a determination of sleeper types based at least in part upon that analysis. As mentioned, this can include an analysis of any potentially sleep-related data that can be collected, detected, or otherwise provided by any of a number of sources. For example, a wearable computer or sensor may be able to provide information such as motion, activity level, breathing patterns, heart rate, blood chemistry, skin temperature, ambient temperature, and body position data. A device with a camera or microphone, such as a smartphone, may be able to provide sound, image, or video data, as well as any other data that can be captured by a sensor of that device, such as may include ambient light, geolocation, pressure, room temperature, and activity data. Another smart or connected device in the vicinity may be able to provide additional data, such as motion, activity, weather, humidity, device state, user state, and other such information. A user may also provide various types of information through one or more interfaces, such as may include information such as gender, age, ethnicity, medical history, current medications, mental state information, physical activity level, and so on. At least some of this information may also be able to be obtained from one or more other sources, such as a user account, public database, medical database, genealogy database, or third party source.

Figure 2:
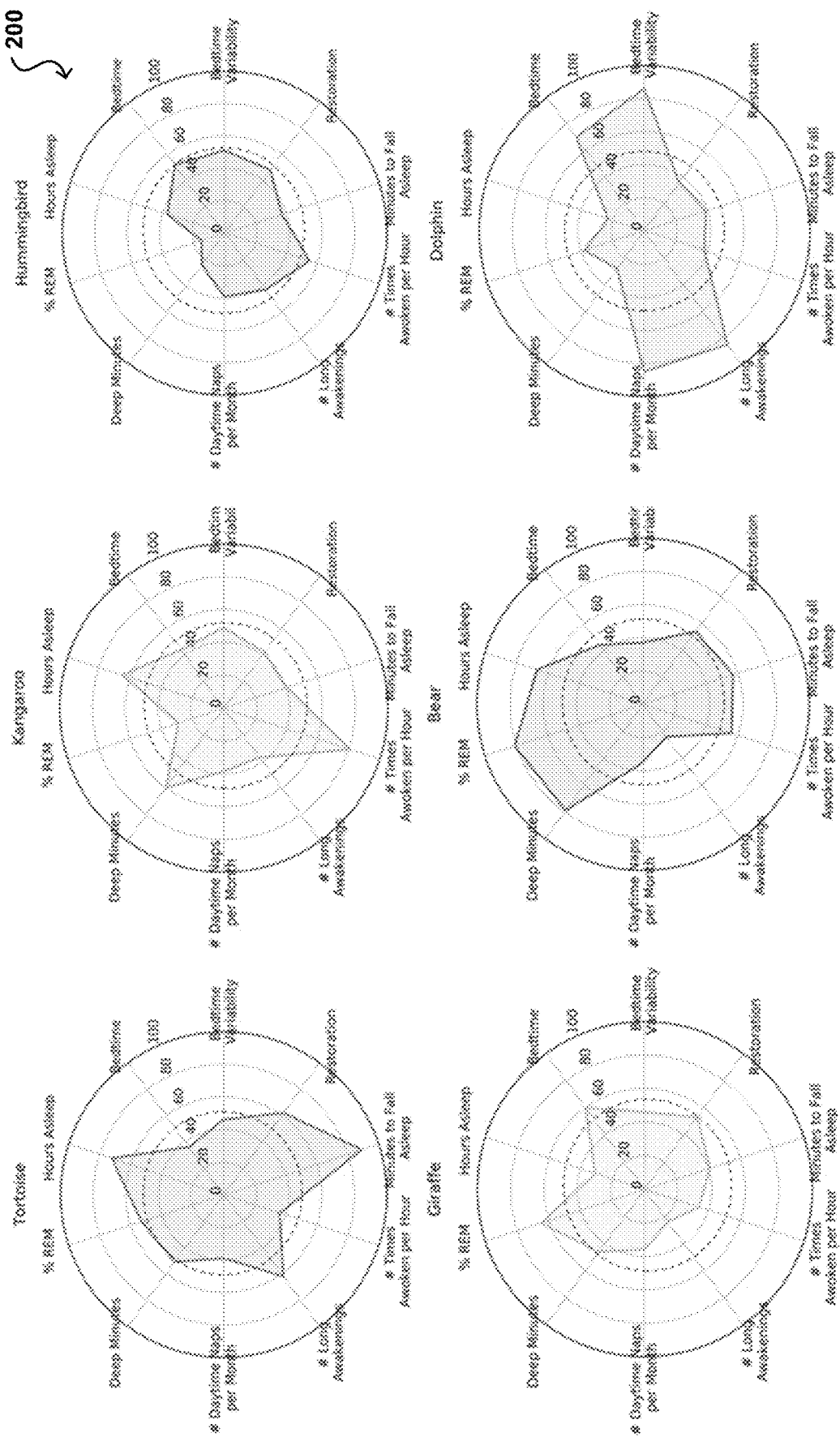
FIG. 2 illustrates example sleep clusters that can be generated in accordance with various embodiments.

In at least some embodiments, any or all of this data can be aggregated for analysis. This data can be analyzed using various approaches to attempt to select data to be included in the analysis. The selected data can then be further analyzed to attempt to reduce a dimensionality of the dataset. For example, the data can be processed to attempt to eliminate redundancies in the dataset. An attempt can then be made to reduce the dataset to a relatively small number of factors that are particularly indicative of different sleeper types. In at least one embodiment, this can include performing clustering using one or more clustering algorithms, such as k-means clustering, with different clustering parameters. This process can be continued, iteratively, until a relatively small number of clusters is obtained that are sufficiently distinct from one another. FIG. 2 illustrates a set of radial plots 200 illustrating an example collection of sleeper types that can be utilized in accordance with various embodiments. In this particular example, clustering resulted in six distinct sleeper types. These types were determined using 10 sleep parameters that are determined to be most important, or at least significant, in determining sleeper type or quality. As mentioned, other numbers and selections of sleep parameters can be used for such purposes as well. In at least one embodiment, additional parameters may be used to determine the clusters or types, then the number of most important factors used to distinguish between those types.

A visualization such as that in FIG. 2 can be provided to users to enable the users to compare values for their sleep animal, or other sleeper type, against those for other sleep categories. For example, a user who is a "tortoise" type in this example takes the longest time out of all these animals to fall asleep, but then wakes up relatively few times per hour. Without the ability to visually compare the plots for these different types, a user might not know how to interpret just the data for that user's sleep animal or compare that to data for other animal types. Further, a user might think they have a different sleeper type, but can help see from these comparisons why a user might more accurately be provided with a different sleeper type. Further, information can be provided to the user that the user's perception may be misleading, as the user is asleep for most of the time and is only aware of a small portion of the overall night of sleep.

Figure 3:
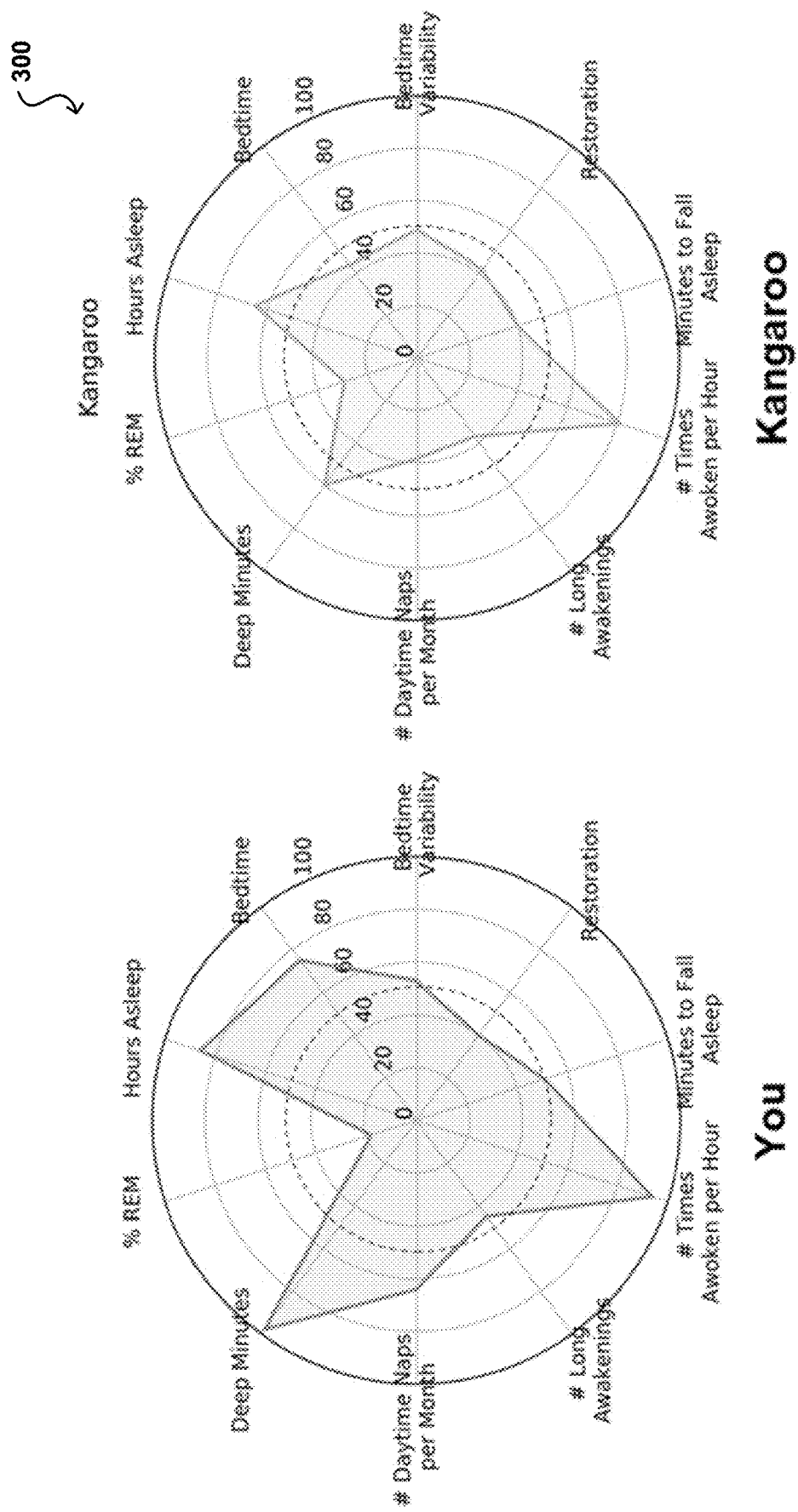
FIG. 3 illustrates example radial graphs for a specific user and a corresponding sleeper type that can be generated in accordance with various embodiments.

While such a visualization may provide insight for a user as to how that user's sleeper type may compare to other sleeper types, the visualization may not provide adequate information as to how the user compares to other animals of the same sleeper type. Accordingly, the user can be provided with a visualization 300 such as that as illustrated in FIG. 3. In this example, the user is provided with a plot (on the left in the figure) that shows the sleep metric values for that individual user, as well as a plot (on the right) that illustrates the average values of users of that specific sleeper type, here a kangaroo. It can be seen that the general shape of the plots is somewhat similar, such that a user can understand why the user was classified to have that particular sleeper type. When displaying these plots together, however, a user is able to understand how the sleep of that user compares against other users of that same sleeper type. For example, the user can determine that the restoration value of about 30 is typical for users with this sleeper type. That same user can determine that this user gets many more minutes of deep sleep than the average user, being near the $100^{th}$ percentile, but also gets significantly more deep sleep than the average user of this sleeper type, which is around the $50^{th}$ percentile. The user can also see that this user goes to bed much later than the average user of this type and tends to sleep significantly longer. Based on this type of comparison, a recommendation might be made that the user try going to bed earlier or getting fewer hours of sleep, to have a pattern that is more typical for users of this sleeper type. While this user has lower than average restoration, that is typical for a user with this sleeper type so attempting to increase restoration may not be as beneficial for a user with this sleeper type. In some embodiments, a user may be able to view comparisons between of plot of that user's sleep metrics versus sleep metrics of different sleeper types, such as others illustrated in FIG. 2, to see how that user compares to other sleeper types as well. If there is a type of sleeper that the user would like to be, then the user can see how that user's sleep metrics differ from those of the target sleeper type, and can attempt to make adjustments according to those differences.

Such presentation can help to overcome deficiencies in prior approaches at least for the fact that this can help convey to a user whether an overall sleep pattern or state should be considered normal. This can also help to visualize whether specific sleep metrics should be considered to be normal, relative to others in general or others of the same sleeper type. This can help users determine whether or not they should be concerned based on any of these values, and whether a change can or should be made. In at least some embodiments, a recommendations engine can be used to provide context as to which goals are attainable in the short- and mid-term for that user. This and other such information can be provided as part of a sleep biography for a user, which can help inform a user as to things that the user is doing well, as well as things that may be able to be improved upon. Such an approach can also provide at least some amount of context for how others compare to this user, as well as what those users may have been able to improve and what worked for other users of the same sleeper type.

In one example, over a thousand sleep-related features were analyzed that can help to describe how a person has slept over a period of time, such as the last month. This data can be analyzed, such as by using sleep experts and data analysis, to attempt to select values that are most relevant for sleep assessment, such as the times when a person went to bed and the number of times that person woke up overnight. This large collection of features may then be able to be reduced to a significantly smaller number, such as around 50-75 feature values, or 64 in one specific example. As mentioned, these features can be selected based at least in part upon what the data shows to be important and what sleep experts believe to be important. This selection of data can also be made based on the quality of clustering that can be performed based on those features. As mentioned, various clustering algorithms can be utilized, such as may include a k-means clustering approach where selected features are projected into a feature space and the Euclidian distances utilized for clustering. In at least some embodiments, clustering may be optimized for aspects such as interpretability, compactness of individual clusters, or separation between clusters. In various embodiments, an approach such as principal component analysis (PCA) can be used to take the selected features and reduce the dimensionality, as clustering can perform poorly in high-dimensional space. In one example, PCA helped to reduce the dimensionality from 64 down to around 22 principal components, and then clustering was performed on those principal components. A set of heuristics or rules can then be applied to finalize the sleeper types based on these clusters. Instead of showing all relevant features, a subset of these features (e.g., 10 features) can be selected to surface to users with sleeper type data. These selected important features can correspond to advanced sleep metrics, the ones determined to be most important for assessing and/or understanding sleep. At least some rules may be applied to select or adjust a sleeper type indicated for a user where a user may be similar to two different sleeper types, or does not have a dominant sleeper type association.

Figure 4:
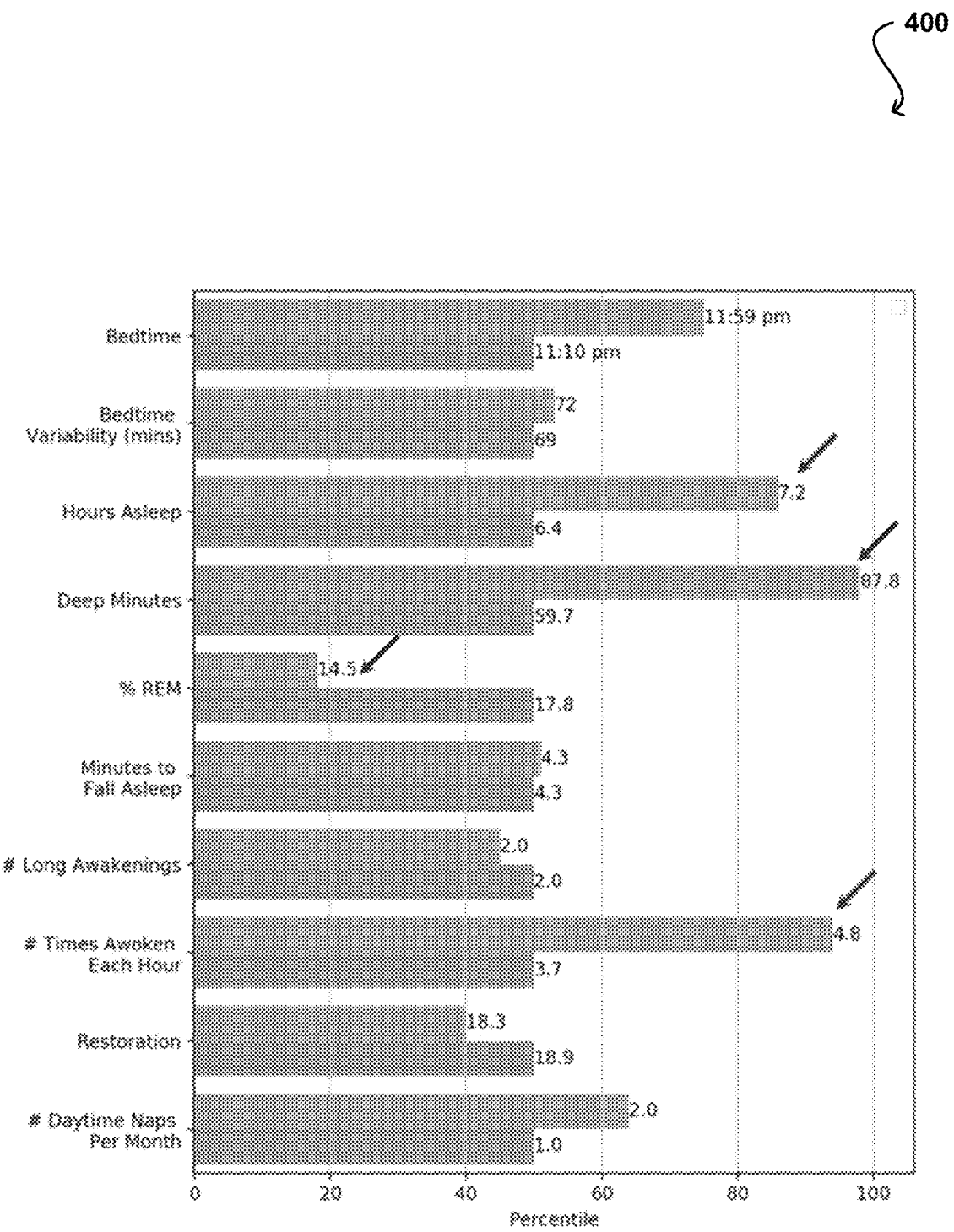
FIG. 4 illustrates example comparison sleep data that can be provided in accordance with various embodiments.

Various other types of visualizations can be provided as well. For example, instead of a multi-dimensional plot as in FIGS. 2 and 3, a user may prefer to obtain a visualization or report that more directly compares specific sleep metrics for the user with values for average users, or even users of a given sleeper type. One such visualization 400 is illustrated in the graph of FIG. 4. In this example, user values are directly compared against average values for each individual sleep metric. Such a visualization may provide at least some users with a more straightforward way to quickly determine those metrics (e.g., bedtime, hours asleep, deep minutes, and number of times awoken) where the user is significantly higher than average and those (e.g., % REM) where the user is significantly lower than average. Further, this graph indicates what the average value is for each sleep metric. A user may be able to select or view different types, and may be able to provide preferences or favorites that can be used to present such information to the user in the future. A user may also have the ability to indicate which formats are not desired by that user, and may have at least some ability to customize these presentations, such as to compare user values, average values, and average values for a given sleeper type on the same graph.

As mentioned, this information can be provided as part of a personalized sleep analysis, summary, or biography. In addition to provide sleep metric values and sleep animal visualizations, information can be provided that can indicate to a user specifically what that user is doing well, and what may be able to be improved. The information may also indicate, for things the user may not be doing well, or where differences may be significant, which approaches may help to improve those things, based at least in part upon data collected for that user and what has worked well for other users of the same, or a similar, sleeper type. While percentages are provided in various examples, other types of data may be provided that may be useful for a user, such as to indicate the number of minutes of each type of sleep that the user averages versus number of minutes on average for across all users and across users of a given sleeper type. Information can also be provided as to why each of these sleep metrics is important, and a goal value for an individual user. Trends can also be identified, and predictions made, and recommendations can be provided to help avoid any undesirable trends or predicted values. In some embodiments, predictions or abnormal values may trigger an interface to request information from a user that can help to narrow down potential causes or help generate more targeted recommendations. This can include asking about things like stress, pain, caffeine or alcohol intake, eating patterns, and so on, which may be otherwise difficult to determine through monitoring data.

As discussed herein, such information can be at least partially collected from, and presented using, a device such as a wearable monitoring device 502. This can help to reduce barriers to gaining the sort of data necessary to conduct a meaningful analysis of sleep state, as a wearable device can more frequently gather data points and have such an analysis performed on a regular basis, even multiple times in a given day, which allows relationships to be determined, such as sleep state when caffeinated, how sleep is based on activity and/or food consumed, and how much stress the user is under. Such a device also enables this sleep data to be collected over a period of time, such as many days, weeks, or months. Data collected over longer periods can help to provide better average values or ranges for various sleep metrics, and can also help to identify trends or patterns in sleep. Such data collection can also help to determine whether data for a given night is typical or atypical for a given user, which can help to put any collected data in context. For a sleep study that only captures one night of data, for example, such determinations are generally not possible, which could then limit the accuracy of that analysis.

Figure 5A:
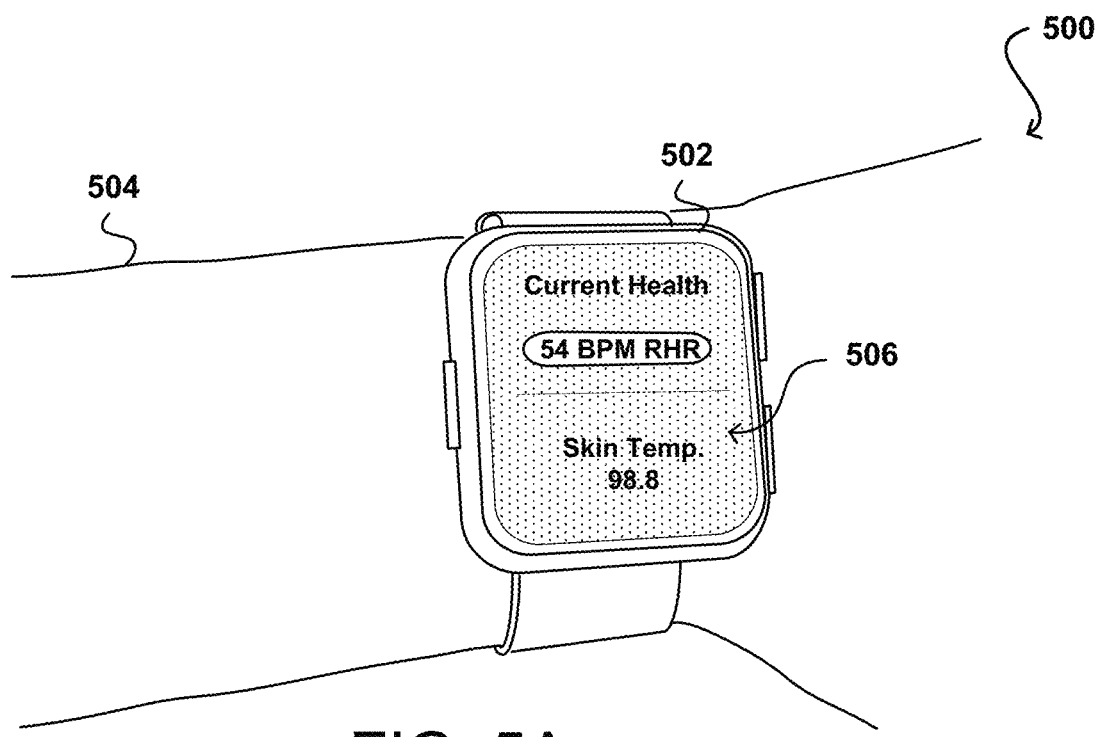
FIGS. 5A and 5B illustrate an example display and sensor configuration that can be utilized in accordance with various embodiments.
Figure 5B:
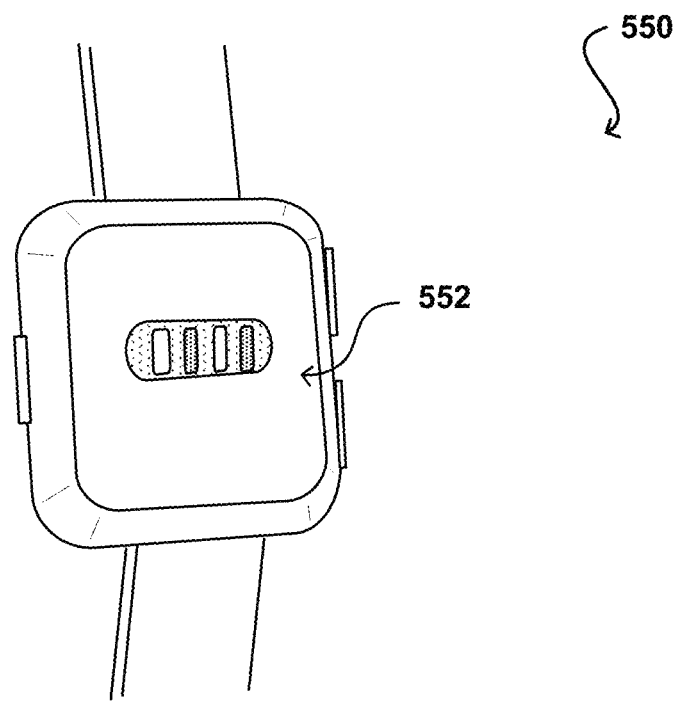

In one embodiment, a user can wear a monitoring device 502 containing components such as an optical measurement sub-system photoplethysmogram ("PPG") component 552 and an accelerometer. The PPG can obtain volumetric measurements by illuminating the skin, such as by using one or more emitters and one or more detectors on a side of the device proximate to the wearer's wrist, such as illustrated in FIG. 5B, and measuring a change in absorption of the light over time. The frequency of these changes can be representative of the heart rate or pulse of the user. Because these measurements can be susceptible to motion effects, it may be preferable in at least some embodiments to attempt to determine the resting heart rate (RHR) of the user. This may be accomplished at night, while the user is sleeping, for example, although other periods of low activity (or even periods that are activity-independent) can be used as well within the scope of the various embodiments. The monitoring device 502 can determine the heart rate by, for example, detecting peaks in the optical signal. In some cases, there may be no clear peaks such that a heart rate cannot be reliably detected, as may be due to excessive motion. For monitoring devices 502 including an accelerometer, inertial sensor, or other such sensor or component, periods of excessive movement can be determined and then excluded from analysis. In other illustrative embodiments, the data for these periods may still be utilized, but with the motion effects accounted for in the analysis. A sensor such as an accelerometer can also be used to determine the overall sleeping period (e.g., from 11 p.m. to 7 a.m.). An estimate of the user's RHR can then be calculated. In one embodiment, a histogram of heart rate values overnight can be generated. A specified measure, such as the tenth percentile of this histogram, can then be taken as a representative value of RHR. The RHR values can be determined in other ways as well, such as by only using time segments where the user has been still for at least a minimum period of time, such as at least five minutes, and the optical signal as a sufficiently high signal-to-noise ratio. An RHR value, once determined, can be used to characterize the overall day for that subject, including periods of sleep. A monitoring device may include other sensors or detectors as well, as discussed herein, such as a temperature sensor that can be used to measure skin temperature, which the device can then display to the user through one or more additional displays of health-related data 506.

The physiological data captured can include any potentially relevant data, including but not limited to heart rate (HR), RHR, $SpO_2$, hemoglobin concentration, water retention, skin sebum or collagen content, lipid content in blood or interstitial tissue, sleep logging, sleep quality, sleep duration, sleep stages architecture (including, but not limited to, time from sleep onset, total time in bed, total awake time), HRV metrics during the day and during sleep, HR-derived metrics, time spent in different HR zones, breathing rate, active minutes, exercise logging, altimeter changes, step count, food logs, water logs, weight measurements, body mass index, body impedance analysis, mood logs, symptom logging, changes in time zones, location, body basal temperature, oral temperature, in-ear temperature, hormonal levels as detected by urine or blood test samples, and the like. In one example, data for RHR and hemoglobin concentrations can be collected using a selection of optical sensors as discussed herein, although other approaches can be used as well. It should be understood that the data discussed herein are merely by way of example and that other combinations or types of metrics and information can be used as well within the scope of the various embodiments.

Figure 6:
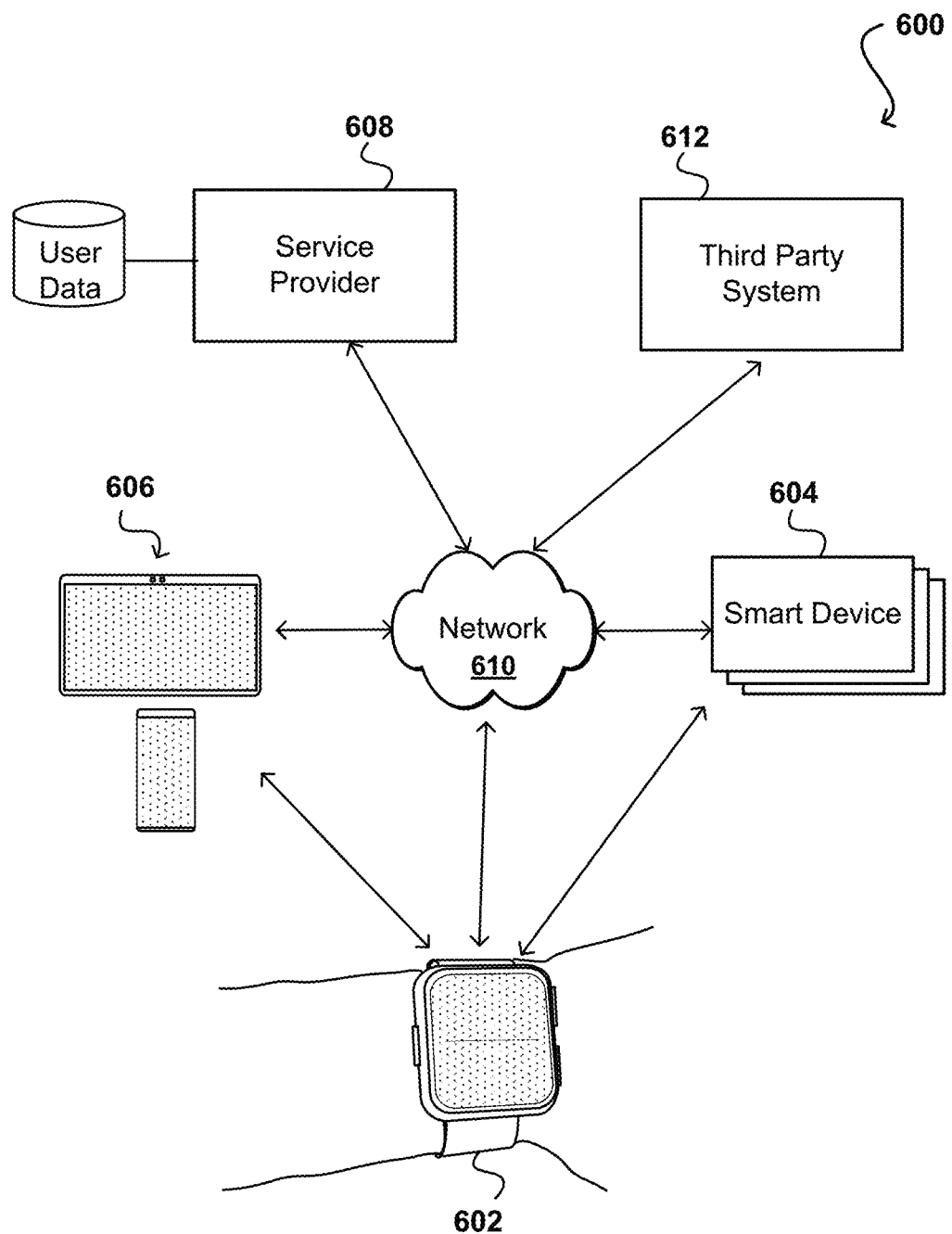
FIG. 6 illustrates example device interactions that can be utilized in accordance with various embodiments.

In at least some embodiments, sleep-related information determined for a user can be presented to, or provided for, a user or related entity in a number of different ways using a number of different devices or communication channels. This can include raw data for analysis or the results of such analysis, among other such options. In at least one embodiment, sleep-related data may be collected or determined using a device such as a wearable monitoring device 602 worn by a user or a computing device 606 associated with the user, as illustrated in the system overview 600 of FIG. 6. In at least some embodiments, such data may also be collected by one or more smart devices 604 associated with the user. Such smart devices can include any device able to collect or determine data that may be useful in sleep analysis, or other such health or state analysis, and provide that data in some way to another computing device, such as through a wired or wireless connection, where that connection may be direct, across at least one network 610, or through one or more other devices or channels. The smart devices may include, for example, a smart thermostat able to provide temperature data, a smart television able to provide state data (e.g., on/off state, brightness, volume, blue light state, or type of content being displayed), a smart alarm able to provide setting data, a smart refrigerator able to provide access data, and other such devices. In at least one embodiment, this data may be collected for analysis by a user computing device 606, such as a tablet or desktop computer running an application with sleep analysis functionality. In at least some embodiments, at least some of this data can be provided to a service provider system 608 associated with the health monitoring device 602 or health monitoring software. In some embodiments, a user may instead subscribe to a service offered by this service provider 608, which can then receive data and provide sleep-related analysis or recommendations. Some embodiments may also utilize a third party system 612 or service for at least a portion of this data collection or analysis, or to collect related data useful in the analysis. For example, this third party system 612 might provide sleep data for other individuals, updated sleep analysis, and so on. In some embodiments the third party system 612 may be associated with one or more of the smart devices 604, and can provide data that is collected by those devices and provided to the third party system. For example, a smart alarm system that can provide information about door and window openings, motion, smoke, and other such data may provide that data to the third party security system 612, and then the third party security system may provide at least some of this data to a sleep-related service provider 608 for analysis, if permitted by the user and under local privacy laws, etc.

Such an approach has various advantages, as multiple types of devices 602, 604, 606 can be used to collect data that may be relevant to the sleep of an individual. This data can then be transmitted over at least one network 610 to a device, system, or provider that is able to aggregate and analyze this data to determine various sleep-related metrics and other such information. Such an approach is also beneficial because the devices used to collect and transmit this data do not need to have substantial processing or memory capacity, since the majority of the data analysis and processing can be performed by the remote system, service, or device. Such an approach can also be beneficial at least for the fact that this service provider can also collect data from devices for other users or individuals, which can allow for a more accurate comparison against others for similar periods of time.

Results of such sleep analysis, or other health or state analysis, may also be provided back to any of these or other such systems, devices, services, or providers. For example, data or instructions may be provided to the smart devices 604 to adjust a state or perform a task, such as to reduce a volume on a television or to dim the lights in a room. In some embodiments data or instructions might be provided to a central system or device, such as a management device, which may then send individual instructions to relevant devices to perform specific tasks or make specific changes. Data or instructions may be provided to the monitoring device 602 being worn by a user to provide prompts or recommendations to the user that should be relatively instantaneously received. Data or instructions can also be provided to a user computing device 606 for presentation to a user, such as to provide updated sleep animal or animal state, changes in sleep metrics, recommendations for improving sleep, and so on.

In situations where a user may live in a smart home, or at least a home that has smart features or devices that may or may not have a centralized control system, at least some of this smart data can be captured for sleep analysis. Further, instructions or recommendations can be provided for at least some of these smart devices or features based at least in part upon the results of the sleep analysis or predictions. For example, a home might have a smart controller (whether a standalone device or software executing on a computer inside, or external to, the home). This controller may be able to interface with a number of smart devices, or at least network-connected devices. This network may be provided using one or more networking or communication protocols or channels, as may include Wi-Fi, Bluetooth®, direct wired or wireless connections, infrared communications, near-field communication (NFC), and so on. These devices can include any devices capable of providing data that may be useful in making sleep determinations, or taking action based on one or more instructions generated in response to sleep-related data. Such devices may include, but are not limited to, smart appliances, televisions, speakers, security systems, monitors, sensors, and the like. These devices may provide various types of data that may be captured or otherwise determined, as may utilize one or more sensors or other such mechanisms, such as may include temperature, pressure, motion, light, sound, color, operational state, changes in device state, and so on. These devices may also make changes based upon instructions received from a sleep monitoring application or central monitoring service, which may relate to desired changes related to current or future sleep state. This may include, for example, adjusting an operational state, changing a configuration, turning on or off, etc. Causing a device to make at least one adjustment can include providing or execution of instructions, requests, or calls, using software and/or hardware resources. This may include using circuitry, mechanics, or electronics to perform a task that impacts a function, state, or operation of a device, system, service or process. As mentioned, this may include providing instructions within a device or system, to a separate device or system, or across a network, among other such options. There may also be various types of adjustments made to a device or component, such as for a display to change the activation or brightness of that display, or to change the content presented via that display, among other such options.

For example, if a user is determined to be going to bed too late or having trouble going to sleep, instructions could be sent at an appropriate time to one or more smart devices to attempt to help the user fall asleep. This could include causing a smart watch or fitness tracker to vibrate, sound an alarm, or otherwise provide a prompt or notification, as may involve animating a relevant sleep animal yawning or getting ready for bed. If a user is watching a connected smart television, instructions could be sent to lower the volume, reduce the brightness, and go into a display mode with lower blue light content. If dimmable smart lights or plugs are connected, an instruction could be sent to reduce the brightness of the lights. Other types of instructions can be sent as well, and these can be sent for single instances or for actions to be taken over a period of time, among other such options. If a user is instead attempting to get less sleep or wake up earlier, instructions could be sent to activate a coffee maker, activate a media player, or turn on lights to attempt to help the user wake up.

In at least some embodiments, these instructions can be determined based not only on a sleeper type or sleep goal, but also based on a current sleep or health state of the user. For example, if a smart alarm is set to go off at a certain time but the user is in a state of deep sleep, or REM sleep, and the user does not desire to be awoken from such a state, then the alarm can be delayed (as permitted by the user or schedule) to a point where the user is awake or in light sleep. Similarly, if actions are to be taken at a certain time to help the user fall asleep, but the user is already asleep, then at least some of those actions may not be taken at this time. Some actions, such as turning off lights, may still be taken, while other actions, such as triggering a sleep notification, may not be taken. For some devices, other actions may be taken based on sleep state, such as for a smart light to turn off instead of reduce brightness if the user is already asleep and does not need help at this time to fall asleep. Various other changes can be made to one or more devices in an environment associated with a user, including environments in which the user is not currently located. For example, if a user is on his or her way home and should try to fall asleep shortly after arrival, devices in a smart home can activate, deactivate, change an operational state, or adjust at least one setting corresponding to that desired goal. This can include, for example, adjusting to a cooler temperature for sleeping, adjusting lights to a relatively low brightness, turning on soothing music, turning off anything that might distract the person, and so on. Adjustments may be made automatically to a smart watch or wearable device as well, such as to provide a prompt or notification that the user should attempt to get sleep shortly. In some embodiments, at least some of these changes may not occur automatically, but may occur in response to a prompt to the user based on that desired goal. For example, if the user is arriving with a guest the user may not wish the smart home to enter a sleep mode. If the system has access to a calendar or task list for the user and can determine that there is a targeted activity or event, the system can use this to determine not to enter a sleep mode but instead to enter a default mode, guest mode, or other such mode. If a determination can be made, such as by using audio or video data, that the guest has left, then the smart home may determine to enter sleep mode at that time.

In some embodiments, adjustments may be made to not only help a user fall asleep or to wake from sleep, but also to attempt to improve or adjust the sleep of a user based upon determined sleep-related data. For example, if a user in a given night is experiencing more light sleep than usual, or keeps waking up, the system may make adjustments to help that user go back to sleep or enter a deeper sleep state. This may include, for example, adjusting a temperature, activating a sound machine, adjusting a setting (e.g., firmness) of a smart bed, adjusting a brightness of a night light, and so on. As mentioned, at least some of these adjustments may also be based at least in part upon information known for that specific user or determined to be relevant for a particular category of sleeper. The impact or effectiveness of such changes can also be monitored over time in order to make changes that are more appropriate for this individual user, and aggregating information across users in general or based on sleeper type.

As mentioned, in various embodiments some of this functionality can be performed automatically, while some of this functionality might require manual instruction or confirmation. This may include providing a recommendation for a user to take an action, or to approve the taking of such an action. The actions taken by the user, and then the impact on sleep state or other health state, can then be monitored over time to attempt to make better recommendations. This may be based upon not only the actions that this user is likely to take, but also the impact of those actions once taken. In some embodiments, machine learning can be used as discussed elsewhere herein to attempt to infer actions to be taken based, at least in part, upon such information. Prompts to a user can take various forms, as may include sounds, audio, video, image data, vibrations or haptic feedback, and so on. These prompts may be provided by a wearable computer or any appropriate device that is capable of receiving or determining the need for a prompt and then providing an appropriate prompt, notification, or presentation. As mentioned, a computing device such as a smart phone or tablet computer will often be in communication with a wearable device or monitoring system, as well as one or more other smart devices, and this information can be provided via that computing device as well. If possible, determination of a device being actively used by a user can help to make a better decision as to the device or mechanism to be utilized for a notification, for example, as being more likely to be received by the user. The type of notification or prompt provided may also be based at least in part upon the capabilities of the device providing the prompt or allowing for the confirmation, as a smart button providing only press information will be able to only provide binary data, such as a confirmation or no confirmation, while a tablet computer can provide for much more granular input. If a smart device is able to provide information about an activity in which a user is engaged, such as a user playing a game, watching a movie, or browsing the web, the device can cater the recommendation and prompt to be presented in a way that is most impactful based at least in part upon the type of activity. Information about this activity can also be used to determine actions to be taken, such as to lower a volume, suggest changing to a different game or movie, and so on. This activity information can be combined with health data as well, such that if a user is playing a game and has a high heart rate, a recommendation may be made to at least take a break from the game to put the user in a more relaxed state if the user is to attempt to fall asleep in the near future. If a user is listening to music, a media player might automatically adjust a playlist to play more (or less) relaxing music, or a different type of music. In at least some embodiments, health data such as heart rate or breathing patterns can be used to monitor the impact of these changes and make further adjustments as appropriate. Statistics about that activity, such as screen time or type of activity, can be used to attempt to determine sleep-related patterns or factors as well, which can help to determine or recommend actions to take to improve sleep or other health-related aspects.

In at least some embodiments, these recommendations, prompts, or changes may be based at least in part upon location. Data, such as geolocation data, may be available that can enable at least certain determinations to be made, such as whether the user is at home, at work, on vacation, and so on. Recommendations or actions may vary based at least in part upon this location data. This can be based at least in part upon the fact that there will likely be different devices available, which may or may not be accessible for making changes. In such instances, a prompt to a user may be made instead of an action. If a user needs to stay up later and is at a friend's house, as may be able to be determined from user contact information, the device might recommend to the user to ask to turn up the volume or brightness, or suggest to play a game or other activity. If the user is in a store, however, such actions may not be possible, such that other recommendations might be made, such as to walk faster. In such an instance, a communication may alternatively be provided to the user that the user should start thinking about falling asleep, or staying awake, and may want to take appropriate action, even if the device or communication does not provide actual recommendations as to the action(s) to take. This location data can also be used to determine possible states for a user, as a user should not fall asleep in a store or while driving.

In at least some embodiments, a device or application may be able to connect to different systems or environments at different times or locations, and the actions or recommendations may be made or adjusted based at least in part thereon. For example, a user device might be able to connect to a smart home when the user is in, or sufficiently near, that smart home, such as when the device can connect to a user home network or can determine proximity using geodata. That user device might alternatively connect to a network in a user's car, and can access smart features in that car. Similarly, the device might be able to connect to a network at work, or may be able to determine that it is in a location with Internet-connected devices or functionality. In any of these locations or environments, the device might be able to determine available functionality, as well as the type of data that is available or can be collected, and can make recommendations or take actions based at least in part upon the type(s) of functionality available in a given environment.

In some embodiments, a user may not be prompted with recommendations, but that information may instead be provided for access by a user at a time that is convenient for the user. This may include, for example, providing information or tips through an interface of a health application available through a computing device or network-connected interface. For example, a user might access a sleep bio determined for that user, that provides the sleeper type and related data for that user. This bio may provide easy to understand information as to the things the user is doing well, such as getting enough sleep and enough minutes of deep sleep, as well as the things the user is not doing well, such as going to bed too late and waking up too often. For areas that can be improved, recommendations can be provided that can be appropriate for that user based on data collected for that user as well as the type of sleeper that has been determined for the user at the current time. This may include, for example, making changes to an environment that are generally beneficial to improving that aspect of sleep, at least for a given type of sleeper. In some instances, there may be recommendations that can benefit from additional information. As mentioned, however, some recommendations may be offensive to some users, such that it may be desirable to ask for additional information. For example, instead of recommending to someone who does not drink alcohol that they cut down on alcohol before bed, an interface might prompt a user to select which of a set of beverages a user is likely to consume before bed, which might contain several options such as coffee, soda, alcohol, water, or other such drinks, worded in a way so as to reduce potential offense, and this information can be used to help determine the relevance of specific recommendations or to better determine health or state information of that user. Information may also be provided as to why consuming certain beverages or foods can be particularly impactful for a particular sleeper type. If a device such as a smart refrigerator is able to determine, such as by scanning a barcode, that a user typically drinks beer before bedtime, then this information can be used to make such inferences and recommendations. Asking questions of a user can be beneficial for other reasons as well, such as to collect information about actions that the user might have taken (where that information may not otherwise be available) and the user's impression of whether those actions made any difference, and if so to provide information about that difference. Such information can also help to better understand the user and to make better recommendations, including not only actions that are more likely to help achieve the desired goal or result, but also actions that are actually likely to be taken by a user at a given time, location, or state.

In some embodiments, a user interface such as a dynamic sleep bio can attempt to collect information from the user in a number of different ways, such as by asking the user questions at specific times. This may include asking for specific data when it is determined that the data will help with a specific determination, action, or recommendation, or may include collecting data over time that may be helpful in understanding a user while not overwhelming that user with questions or actions. In some embodiments these questions may be questions with simple yes/no answers that can be handled via a device that may have a limited interface, such as a smart watch or fitness tracker with a small touch screen. In other embodiments, these questions may be presented when a user accesses a corresponding app on a device with more resources and interface capability, such as a smart phone or tablet computer. In one embodiment, one or more surveys can be designed that can help to assess whether information in a content presentation such as a sleep bio helps users understand how they sleep and how they could improve their sleep. This may include, in one survey or over a series of smaller surveys, asking questions about whether users understand their sleep animal independent of the advanced metrics, whether the advanced metrics are confusing, what other sleep animals may relate to a user, whether users think they should have different sleep animals, whether specific types of charts or displays are helpful and easily understood, whether a user clearly understands how their sleep differs from that of other users, and so on. Such a survey can help to not only improve the bio content or presentation across users, based at least in part upon aggregated feedback, but can also help to customize the bio for a specific user, such that the user is presented with a selection of information that is most helpful for that user, and that the information is presented in a way that is helpful and well received by the user. As mentioned, a sleep bio can help to engage users on a new level about their sleep. This presentation of information can help users better understand the types of sleepers they are, and can help them understand what they can do to sleep better.

In some embodiments, a short survey or even a single question may be presented at a specific time to identify a particular activity. For example, a question might ask a user whether they are engaging in one or more activities, such as eating, drinking, or smoking, which may impact the ability of that user to fall asleep in a short period of time. If available and permitted by the user, any audio, camera, or sensor data that can help to identify such activities can be used as well. This can include, for example, a smart refrigerator than can indicate a door was recently opened or food removed, or a smoke detector that detects at least some amount of smoke, and so on. Some activities, such as browsing the web or listening to a podcast, may be able to be determined through a questionnaire or by communicating with a device being used for that activity. One or more questions may also be presented to inquire as to a perception of a user. This may include, for example, whether the user feels tired, stressed, concerned, anxious, wide awake, depressed, and so on. While perceptive data may not end up being entirely accurate, it can be helpful in better understanding the user and making correlations between perceptions and sleep patterns. This may include inquiring about other health information as well, such as whether the user is still, feels certain types of pain, has an injury, is diabetic, is pregnant, is having bladder control issues, and so on. An attempt can be made to gather information about sleep apnea status, twitchiness, disease status, or intake (or prescription) of medication. Inquiries may relate to other issues that are not directly health related but can help in making assessments, such as whether the user is a shift worker or otherwise has a specific sleep schedule, whether the user is in an environment that makes it difficult to sleep during specific hours, whether the user is a parent of a small child that may wake up frequently or randomly throughout the night, etc. This information may also help to make better recommendations to a user, as a user may be less (or more) likely to engage in certain activities or take certain actions if tired, depressed, stressed, etc. A user might also be able to provide information as to whether they think that at the current time they are more like a different sleep animal. This can help to better understand user perceptions, and can be used to tailor recommendations or actions by inferring that by selecting a specific sleep animal the user is inherently providing you with perceived values for one or more sleep metrics that are dominant for that other sleep animal. Any or all of this information can also be used to adjust the weightings of one or more factors in the determination, which may cause the user to be more closely aligned to a specific sleep animal, or be aligned with that animal with more certainty or confidence.

In some embodiments, a sleep bio can provide additional information as to why a user has been associated with a specific sleep animal or health type. For instance, information can be presented that identifies the defining metrics for each sleep animal based on the distribution of the advanced sleep metrics at, for example, the 25th, 50th, and 75th percentiles. The defining metrics can be the "peaks" and "valleys" on the radar chart, so they are the metrics that are typically high or low, even for the 25th or 75th percentiles. Additional information may also be provided for users who are determined to be edge cases, where those users have sleep characteristics that put them "in between" sleep animals, or where the user has characteristics that are similar to two different sleep animals without clearly aligning to a single sleep animal. For instance, if a user has both a high "number of times awoken per hour" value and a high "minutes to fall asleep" value, that user might be classified as a kangaroo or a tortoise. To help decide the appropriate sleep animal or health type for a user, a post-clustering determination can be made based on one or more heuristics that calculate different distance metrics based, at least in part, upon the advanced sleep metrics in a radar chart, or other such multi-dimensional sleep space. In at least one embodiment, such a distance metric can weigh whether users have similar "peak" and "valley" advanced sleep metrics in comparison to sleep animal-related advanced sleep metrics. For instance, the peak for a kangaroo may be the "number of times awoken per hour" metric, so the distance metrics could more heavily weigh the "number of times awoken per hour" metric, ensuring that a user must have a similar "number of times awoken per hour" metric to be associated with a Kangaroo.

Various distance heuristics can be used post clustering. These can include, for example, use of metrics such as a Euclidian distance with centroid distance based assignment, such as may be used in a k-means clustering approach. Other distance metrics can include a Manhattan distance, Chebyshev distance, cosine similarity, Levenshtein or hamming distance, Kendall-Tau distance, or weighted Manhattan distance, among others. In one example implementation, a weighted Manhattan distance is utilized post clustering, which rewards extreme percentiles. In this example, the final sleep animal was determined in part by:

> Final Sleep Animal=Animal with Minimum
> Weighted Manhattan Distance from "Typical"
> Sleep Animal Advanced Metrics Derived from
> K Means Clustering An additional metric was also generated and validated that describes something similar to sleep onset, relating to the time from bedtime to the last wake-light-wake cycle, where a light epoch must be less than one hour. Such an approach can be similar to the latency to persistent sleep, which can help identify individuals suffering from insomnia.

Figure 7:
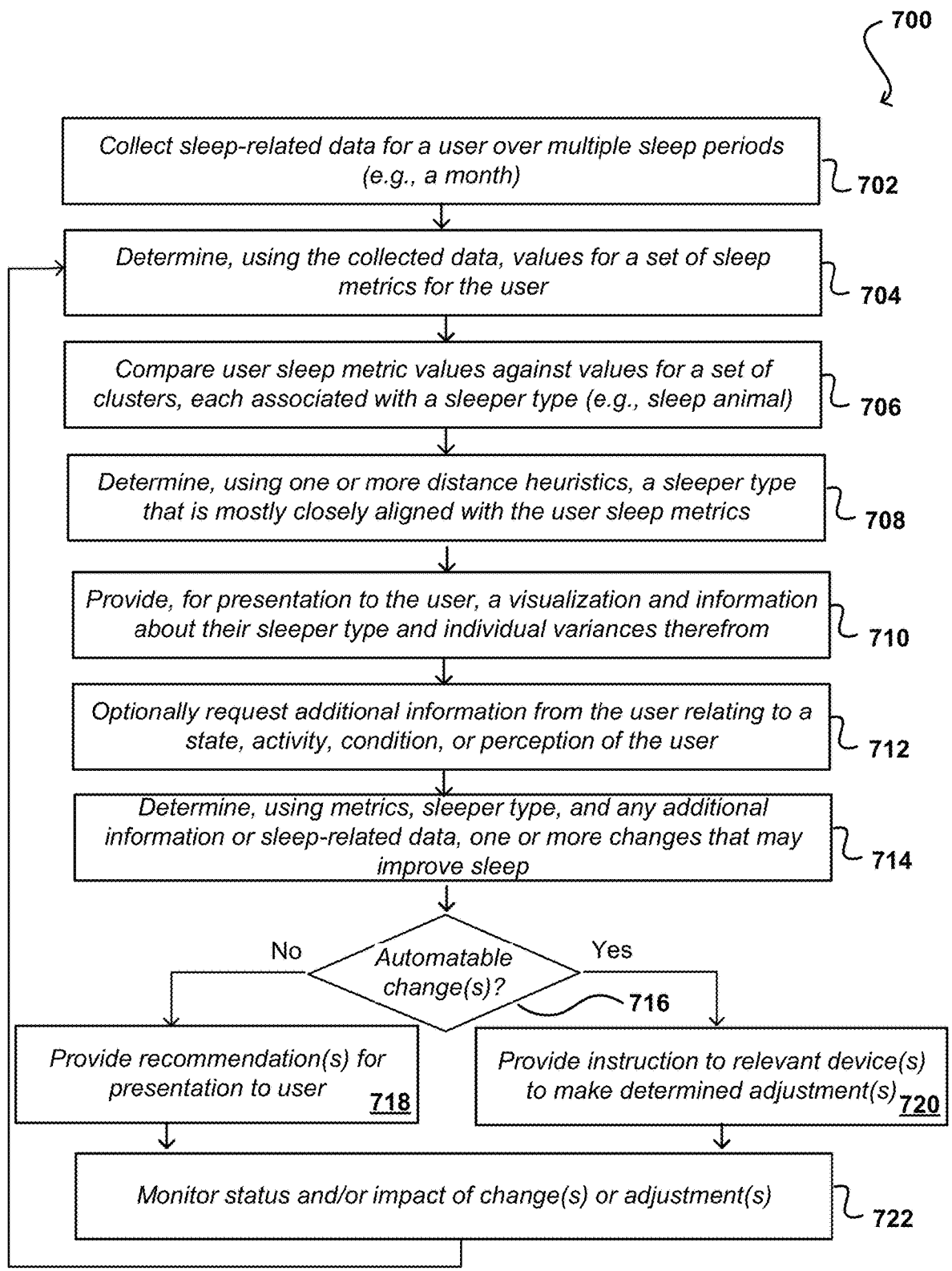
FIG. 7 illustrates an example process for determining, providing, and utilizing sleep data in accordance with various embodiments.

FIG. 7 illustrates an example process 700 for determining sleep information for a user, and making or recommending one or more changes to improve sleep, that may be utilized in accordance with various embodiments. It should be understood that, for this and all other processes discussed herein, there can be additional, alternative, or fewer steps performed in similar or alternative orders, or in parallel, within the scope of the various embodiments unless otherwise stated. Further, it should be understood that sleep is used as an example for explanation purposes, but such an approach can be used for other physical or mental states, conditions, or activities of one or more users as well within the scope of the various embodiments. In this example, sleep-related data is collected 702 for a user over multiple sleep periods, such as over multiple days, weeks, or months. The sleep-related data can include data directly related to user sleep, such as a time when a user falls asleep and a time when a user awakes, but can also include data that may only be someone related to an aspect of sleep, such as a temperature of a room or an amount of noise when a user was in a particular sleep state or transitioned between states. This data can be collected by any appropriate method, such as receiving through direct entry or from a device with a sensor or processor for generating or providing the data. In at least some embodiments, at least some amount of pre-processing of the data may be performed, such as to remove noise, remove redundant data, select relevant data, perform normalization, and so on. The data can also come from multiple sources in multiple locations, such as manual input, device determination, sensor detection, and so on.

At least some of this collected data can be used to determine 704 values for a set of sleep metrics for the user. These may include sleep metrics determined to be particularly important for analyzing sleep, as may include percentage of time in REM, average hours asleep, average bedtime, bedtime variability, average restoration length, average minutes to fall asleep, number of times awoken per hour, number of long awakenings, number of daytime naps per period, and average number of minutes in deep sleep, among others. These user sleep metric values, as well as other potential metrics, can then be compared 706 against values for a set of clusters, with each of those clusters being associated with a sleeper type (e.g., a sleep animal). Each sleeper type can include values determined to be representative of users of that sleeper type, as may have been determined using various approaches discussed and suggested elsewhere herein. Using one or more distance heuristics, or another such approach, one of these sleeper types can be determined 708 or otherwise selected as being most closely aligned with the determined user sleep metrics. As the user sleep metrics change over time, the determined sleeper type (e.g., animal) for that user may change as well. In this example, a visualization and information about the selected user sleeper type can then be provided 710 for presentation to the user, along with information about individual variances from the average or expected values of a user of that sleeper type and other such information. Information can also be provided that contrasts metrics of the selected sleeper type with those of other sleeper types.

In addition to providing a user with information about their sleeper type and their individual sleep data, it may be desirable to provide the user with options or suggestions that may help to improve the sleep of that user, or to otherwise achieve another sleep-related goal. In this example, additional information can optionally be requested 712 from the user that may relate to, for example, a state, activity, condition, or perception of the user, where this information may be relevant for making sleep determinations or recommendations, but may be difficult or unavailable to obtain as part of the otherwise collected sleep-related data. As mentioned, this may include whether the user is currently sleepy or anxious, whether the user engaged in specific activities at one or more points in the day, and so on. Using any or all of the sleep metrics, sleeper type, and sleep-related data or additional information, one or more changes can be determined 714 that can help to improve sleep or achieve another sleep-related coal. A change may involve a change in user action or behavior, or may involve a change in operation or state of a device, system, or service that may have an impact on the sleep of the user. For each of these changes, a determination can be made 716 as to whether the change is one that may be automated, or performed automatically, by a device, system, or service. If not, a recommendation can be provided 718 for presentation to the user to perform a given action, modify a behavior, change an operational state of a device, or otherwise make the determined change. If the change is able to be automated, then one or more instructions (or requests or calls, etc.) can be provided 720 to one or more relevant devices, systems, applications, modules, or services to make the determined change, or perform a task that results in, or corresponds to, the determined change. After a recommendation is provided, or change instruction sent, the status and/or impact of the change can be monitored, such as to determine whether the change was made or an extent to which the change was made, as well as any change in behavior or deviation from predicted sleep occurred. This information can then be provided along with the collected sleep-related data to update the user sleep data, which may result in changes to a determined sleeper type, profile, bio, recommendation, or other such aspect as presented or suggested herein.

Various illustrative embodiments capture and consider objective physiological data non-invasively obtained through wearable monitoring device sensors and logged, such as activity, sleep, heart rate ("HR"), and the like. These physiological data variables and metrics can further include, by way of but some examples, comparable biomarkers such as the user's resting heart rate ("RHR") and/or other HR-derived data, blood oxygen concentration ($SpO_2$) level, heart rate variability ("HRV"), sleep duration and quality, exercise levels, weight, hemoglobin, and water concentration, as well as concentration of oils/lipids/collagen on the skin, among other options. Various systems and methods may additionally or alternatively utilize electrodermal measurements as well as information from other types of devices, such as from a chest band or an electrocardiogram ("ECG") patch. Even specifics and conditions of a user's interaction with his or her wearable monitoring device, smartphone, and/or other devices can be captured and analyzed, such as how often the device is checked and how hard buttons are being pushed.

In an illustrative embodiment, patterns of heart rate, sleep, and physical activity are analyzed by one or more predictive model algorithms, which can vary depending on factors such as system configuration and what physiological objective data is collected and analyzed. In particular, potential categories of objective, physiological data points may include the most predictive ones such as: resting heart rate; heart rate variability; mean steps per day; active minutes; mean sleep schedule, such as when, on average, the user goes to bed and when he or she awakens; length of time before falling asleep, once in bed; number of sleep interruptions; and sleep stages, including amount of "deep" sleep. In at least some embodiments, a user may wear a smartwatch or some other monitoring device capable of capturing at least some of the sleep-related data for determining length, quality, stages, and the like.

The categories and types of metrics may be customized, and the data collected passively, with the user not required to perform any action in order for the data to be transmitted to the cloud or other network. One or more of the health-related metrics can be monitored over time to determine patterns or cycles of variation in the metrics, which can be correlated with mental state. In particular, analysis of how much variation there is within the various categories of inputs will prove helpful in performing various types of analysis presented herein. This information can then be used to update predictive models, as well as to update individual recommendations based at least in part upon the current values of those metrics for the user. Information about the predictions, and updates to the predictions, can be surfaced to the user, which can assist with planning around life events.

At least some of the physiological or other health data can come from multiple devices. For example, a user might wear a "smart" ring capable of providing accurate heart rate information, a wrist temperature sensor that measures both skin and ambient temperature, an oral temperature sensor, or earbuds configured to provide accurate body temperature information. This information can be received and then used with other available data to attempt to generate more accurate results. For example, temperature data from earbuds alone might be used for the tracking at hand, or temperature data from earbuds, a smart ring, and a monitoring device can all be analyzed together, once synchronized in time, in order to remove any temperature variations that are due to external factors, as temperature readings on the wrist may be more susceptible to changes in ambient temperature, etc. The results can be averaged or otherwise collated, or if two of the three readings are consistent with variation but the third is not, then data from the third device can be removed from consideration over the time of variation. Data from other external devices can be used as well within the scope of the various embodiments. For another example, if data is available from blood testing machinery, urine analysis devices, etc., then other information about hormone levels or body chemistry can be used as well in predicting various states and time points. Data such as temperature can be obtained from a number of other types of devices as well, such as may include smart clothing, bed sheets, wearables, and the like. Optical devices for measuring body characteristics, such as chemicals in the skin, through diffuse reflectance spectroscopy, photo-acoustic effects, optical coherence tomography, diffuse optical tomography, time-gated spectroscopy, or spatial frequency domain imaging can be used as well within the scope of the various embodiments. Different aspects of the human body will have different patterns, and these can be learned and applied to the available data to make as accurate a prediction as possible. As discussed herein, machine learning can be used to attempt to improve the accuracy of the pattern recognition and classifications over time.

It should be noted that the selection of, and even the versions of, the sleep-related applications can differ and be customized, depending on the type of user device and storage space and computing limitations thereof; the number of graphical elements displayed may differ between, say, desktop monitors and worn monitoring devices, while the user movements necessitated may also differ (i.e., movement and clicking of a mouse, as opposed to one or more swipes on a smartwatch). A high-resolution screen will permit more information to be displayed. In doing so for a tablet or smartwatch, for example, portions of a touchscreen are predetermined as user input areas, where pixels are responsive to touch. Of course, some interfaces requiring a larger display area may simply not be suitable for a small screen such as that found on a typical smartwatch or even a mobile phone.

In one embodiment, an overnight heart rate recording for a user can first be divided into various sleep stages, such as may include light sleep, deep sleep, and rapid eye movement ("REM") sleep. The HRV parameters and HR can then be calculated for a stage of sleep only, rather than for the entire night, if desired. A model of the RHR (or a metric derived from HRV) calculated only over the non-REM sections of sleep (e.g., light sleep and deep sleep) can be used in connection with predictive models for purposes discussed herein.

In another embodiment, a person's breathing rate can be extracted from the PPG signal. The breathing rate would typically be measured to be between twelve and twenty breaths per minute. An average breathing rate can be extracted for each night or a set of nights. The subject's activity level can also be tracked, which can be used to correct confounders such as heavy exercise and other intense physical activity which may affect the resting HR and HRV parameters used in the predictive models.

Concurrently with the analysis and predictions in at least some embodiments, HR information such as the RHR can be monitored for the user. As mentioned, this may include using the monitoring device 102 during a sleep period and after a minimum period of inactivity to obtain RHR date for the user using one or more approaches as discussed and suggested herein. If it is determined that there is no resting heart rate pattern information available, then the process can continue without utilizing such pattern information.

Again, these HR data and other metrics can be used to predict health issues, and in some embodiments combinations of these metrics and approaches can be used to attempt to improve the accuracy of the predictions. In other embodiments, two or more measurements can be combined to attempt to improve the predictions, whether using user input-based predictions as discussed above or based upon measured or detected body and health data alone. For example, in one embodiment a user's HR information and blood or tissue chemistry can be used to screen for mental state. For example, there may be variations in the concentration or number of red or white blood cells, or the concentration or amount of hemoglobin, ferritin, serum iron, peripheral capillary oxygen saturation ($SpO_2$), water, lipid, collagen, sebum, or other components typically found in a person's blood or skin tissue or the surface of the skin. Variations in body temperature can also be determined using a temperature sensor.

A monitoring device in accordance with various illustrative embodiments can perform non-invasive real-time measurement of hemoglobin and water content (e.g., a hemoglobin to water ratio, or relative changes in just hemoglobin or water concentration in the blood and tissue) in a user's body using optical emitters, sensors, and other components such as those discussed and suggested herein. The amount of light absorption in human skin can vary with differences in hemoglobin and water concentration. This can be particularly noticeable for light having wavelengths in the infrared ("IR") or near-IR spectrums. As the hemoglobin concentration decreases, the amount of light absorption due to hemoglobin decreases. The amount of light absorption will also change by a different amount based on changes in oxygen saturation, and the absorption differences are more pronounced at different wavelengths. Accordingly, in some embodiments a monitoring device 102 might include a first emitter at a first wavelength and second emitter at a second wavelength appropriate for detecting variations in hemoglobin and water concentration, while in other embodiments the device 102 might include a third emitter at a second wavelength appropriate for detecting variations in $SpO_2$, while some tracking devices 102 can include both (or an emitter assembly capable of selectively or concurrently emitting light in both target wavelength bands). In one embodiment, a monitoring device 102 can include two light-emitting diodes (LEDs) with two wavelengths in the range of about 600-1000 nm to detect changes in $SpO_2$ and hemoglobin content, and another LED with a wavelength in the range of 1000-1500 nm for measuring variations in water content, and for measuring hemoglobin to water ratios when combined with one of the first two LEDs.

As with resting heart rate data, values for metrics such as hemoglobin, water concentration, and $SpO_2$ can be cyclical. By monitoring how these metrics vary in the user's body over time, and how these variations correspond to mental state, measurements of the metrics can be used to predict timing of health-related events and episodes. Changes in these parameters also can be indicative or other potential issues in a user's body, and thus can be used in some embodiments to recommend seeing a physician or taking other action.

In some embodiments a software application might ask questions of a user in response to detected changes to the user's body. For example, changes in sleep pattern might be due to changes in location or stress. Other changes, such as new medicines or exercise patterns, might influence at least some of the measurements as well. By obtaining this information, the software can determine whether to exclude certain values or periods of time, whether to weight those values differently, etc. Information available from motion sensors or other activity tracking can also be used to attempt to determine some of these factors as well within the scope of the various embodiments.

With regard to hemoglobin concentration, in one embodiment, the concentration in a user's body is measured using an optical technique such as near-infrared ("NIR") spectroscopy. NIR approaches can utilize an emitter that emits radiation in the NIR spectrum, such as may have a wavelength in the range of 780 nm to 2500 nm. NIR has an advantage over other optical techniques in that it can penetrate the skin further than other optical techniques. Portions of the radiation that are not absorbed can be reflected back to one or more detectors having sensors able to detect radiation over at least the corresponding wavelength band. The absorption data determined by the detector(s) can be analyzed using a multivariate approach, such as principal component analysis ("PCA") or neural networks, among other such options, to determine information about the composition of the blood in the subject's body. One or more optically dispersive elements may be used to separate out specific wavelengths for measurement. In one example, two detectors are used at different positions in order to attempt to account for artifacts in the surface of the skin, as well as variations in the skin that might result from compression or other outside influences. The specific wavelength(s) used to measure hemoglobin and water concentration (e.g., between 900 and 1500 nm) can depend in part upon the specific implementation and design, as there can be a tradeoff between depth of penetration and sensitivity to variations in concentration, as some devices will have less sensitive detectors and some devices will be tight against the skin while some may have an amount of separation. Detectors of different materials, and thus different sensitivities and accuracies, can be used as well, as may include detectors made of silicon and indium gallium arsenide, among other such options. Devices in accordance with various embodiments may also utilize more than one emitter, having different wavelengths of emission, or emitters that emit more than one wavelength, etc. In some embodiments, the accuracy can depend in part upon the orientation of the device relative to the skin, the proximity to the skin, or any compression of the skin due to the device (such as by a tracker being worn tightly around the skin or being compressed by another portion of the body during sleep). Accordingly, in some embodiments a pressure sensor, camera, or other sensor can be used to attempt to account for such factors or variations.

Physiological data can be collected over time, then filtered to reduce noise and random variations in the data, which may be due to natural variations as well as outside influences such as changes in exercise, diet, stress, and sleep. Other types of processing of the data can be used as well as would be apparent to one of ordinary skill in the art in light of the teachings and suggestions contained herein. As mentioned, in various embodiments, measurements can be made during periods of rest or sleep, where there will be relatively few changes in position over a period of time. Changes in oxygen or hemoglobin signals can be triggered by movements or changes in position, such that periods of rest may provide more accurate or consistent results, or representations of the true state of the body independent of many external factors. In some embodiments, a monitoring or other associated device can utilize accelerometers, altimeters, inertial sensors, or other such components to monitor movement, and the device might wait until the subject has been still (within an allowable threshold amount of movement) for at least a determined period of time of inactivity to take measurements. This can provide sufficient time for the levels to reach an equilibrium point, thereby allowing for greater accuracy in at least some embodiments.

The filtered data collected over time can be analyzed to determine or update patterns determined for the respective metrics. This can include inputting the physiological data into one or more predictive models to identify whether the physiological data, including any pattern found therein, correlates with one or more biomarkers relevant to physical or mental state. Biomarkers used for comparison with the physiological data are open-ended and include, but are not limited to, the following:

- Low levels of activity (mean total minutes per day with heart rate in cardio or peak zones; when this biomarker has a lower value, depression risk is higher, for example);
- Variable sleep (standard deviation of minutes asleep per night or standard deviation of bedtime or wake-up time; when this biomarker has a higher value, depression risk is higher);
- High resting heart rate (maximum (or mean) resting heart rate; when this biomarker has a higher value, depression risk is higher);
- Rapid sleep onset latency (mean minutes between bedtime and onset of sleep; when this biomarker has a higher value, depression risk is lower);
- Low mean steps per day (when this biomarker has a higher value, depression risk is higher);
- Long periods or gaps of wakefulness during a sleep period (i.e., highly-disrupted sleep; when this biomarker has a higher value, depression risk is higher);
- Low heart rate variability (when this biomarker has a higher value, depression risk is higher);
- Late bedtimes (when this biomarker has a higher value, depression risk is higher); and
- Slow REM onset latency (when this biomarker has a higher value, depression risk is higher).

The predictive models can update pattern information based on additional data to obtain more accurate pattern information. In some embodiments, the state data may be weighted or decayed such that recent physiological data has more of an impact on pattern determination to account for changes in the health of the user, such as changes in age, hormone levels, and the like. While current information can be sufficient to form a screening or initial analysis, the predictive models will become more accurate as additional information is received and analyzed.

Various algorithms and approaches can be used to analyze and correlate the physiological data within the scope of the various embodiments. Information about the user's body can be obtained by a monitoring device or other such tracking device that can be correlated with mental and physical state and health information. This can include information known across various individuals as a base pattern, but also can be updated or determined for a specific person to provide more accurate predictions. The analyses, correlations, and determinations can be done by advanced signal processing methods, averaging, or otherwise aggregating data obtained over additional time periods and/or by feeding the data into a machine learning algorithm, among other such options. The physiological data can be used to generate predictions based on any determined patterns. Further, as changes in the RHR information are determined over time, for example, predictions can be updated, such as when RHR becomes indicative of a beginning of a depressed or anxious state.

The data can be provided as inputs to a predictive modeling or machine learning process that can use the information to predict future mental or physical states. As mentioned, there may be various physiological data inputs, as may relate to heart rate, activity, sleep, and others discussed herein. Patterns can be determined and used for each available type of data to attempt to come to a more accurate determination. The data values may be weighted by different amounts, such as may be based upon strength of prediction or accuracy, among other such factors. These weightings can be updated or modified over time, such as may be based upon machine learning or changes in a user's body or state, etc. There may also be different confidence levels or other factors that can impact the relative weightings as well. The weight values chosen can also depend on the signal-to-noise ratio of some signals.

Generally speaking, via machine learning techniques (expand), one or more systems may be trained on a set of metrics, physiological data and/or otherwise, for a particular user or a general population. Physiological data and other metrics are then captured from the particular user and analyzed by the trained systems to determine relationships between that user's metrics, and then a mental state status and/or guidance can be pushed to the user.

A machine learning system using a convolutional neural network ("CNN"), for example, can be designed to extract HR metrics during sleep. The CNN can be trained on a data set, such as, for example, during different sleep stages, and the optimal sleep stage can be determined. A long short-term memory neural network ("LSTM"), hidden Markov model, or other time series model can be designed to predict state events based on previous history, this model can also take into account any of the appropriate variables discussed herein. Multiple LSTM models can be trained to predict different factors relating to mental or physical health in various embodiments. Moreover, it is certainly within the scope of the present disclosure to apply feedforward, recurrent, radial basis function, modular, and/or self-organizing neural networks.

As discussed, there might be one pattern generated in some embodiments that is a function of both RHR and sleep data, or other such metrics. In some embodiments a deep neural network or other machine learning approach can be used to "learn" pattern based on the obtained metrics, among other such information. Various other predictive modeling patterns and approaches can be used as well, including those discussed and suggested herein. Correlations and patterns, discerned through the predictive modeling, can be used to predict a timing of a next occurrence of a mental health-related event, as well as potentially other related events as well. The pattern and correlation information may be updated in some embodiments any time additional information is provided or obtained.

As mentioned, the predictive modeling can use and apply various types of information which may impact data values for differing bodies. For example, information may be obtained about the amount of exercise or physical activity a person has undergone during a given day or period, which may account for differences in detected physiological data values as discussed herein. There may also be variations in diet, stress, weight, body fat percentage, body mass index ("BMI"), medication, or other such factors that can be accounted for as well. In at least some embodiments, these and other such factors can be fed into one or more predictive modeling schema and then a regression applied in order to verify conditions for accurate predictions. Should a correlation with one or more biomarkers be found, at least a potential health issue may be determined for the user. The process can continue and repeat, updating the state status for the user, and additional types of information can be added into the process for consideration as the information becomes available. In at least some embodiments, the recommendations or weightings may change over time, such as for changes in the body or exercise levels, age, and the like.

Once the health state status is generated or updated, that can be outputted or exposed to the user or another appropriate or authorized entity. The state status information can be surfaced in a number of different ways. There can be various options through which a user can navigate, or there can be specific interfaces or displays provided, among other possibilities. In some embodiments, the symptoms of various users can be determined and the application can predict when those users will suffer from health-related maladies, with corresponding notifications delivered to the users. A given application might also provide different views depending upon a user's goals. In some embodiments, the app might also provide recommendations for improving health or achieving the goal, based at least in part upon the monitored health information. Recommendations can also be made to see a doctor in cases where the physiological and other data might indicate a potential medical condition.

As mentioned, the various embodiments can be implemented as a system that includes one or more monitoring/tracking devices for a given user. In other embodiments the embodiments may be provided as a service, which users can utilize for their devices. Other fitness tracker and health care providers may also subscribe or utilize such a service for their customers. In some embodiments, an application programming interface ("API") or other such interface may be exposed that enables collected physiological data, and other information, to be received by the service, which can process the information and send the results back to the monitoring or related computing device, for access by the user. In some embodiments at least some of the processing may be done on the monitoring or tracking device itself, but processing by a remote system or service may allow for more robust processing, particularly for tracking devices with limited capacity or processing capability.

Figure 8:
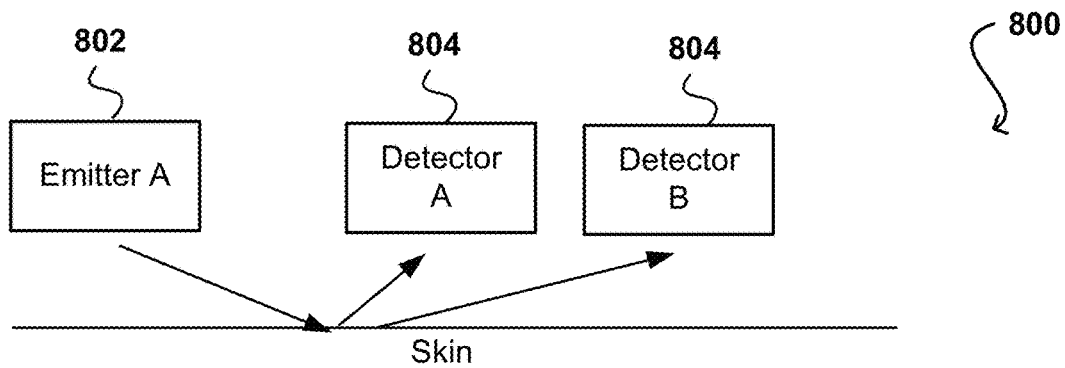
FIG. 8 illustrates example monitoring device light paths that can be utilized in accordance with various embodiments.

As may be seen in the illustrative embodiment 800 depicted with the aid of FIG. 8, light emitted from one or more emitters 802 can be reflected from the skin back to the detectors 804. Although a user in various embodiments may wear a monitoring device, such as a smartwatch or fitness tracker, or another PPG device proximate to a wrist location, in other embodiments such a device may be worn in locations such as the ear, fingertips, ankle, neck, upper arm, torso, leg and/or forehead (e.g., such that light sources of the PPG devices are adjacent to blood vessels of a human). Two detectors 804 are used at differing positions in this embodiment, to account for artifacts in the surface of the skin, as well as variations in the skin that might result from compression or other outside influences.

The path light travels from an emitter 802 to the skin and back to one of the detectors 804 can be referred to as a "light path." In addition to having its ordinary meaning, a light path can refer to the probabilistic path of photons from one location to another, typically from the light source (or emitter) to the light sensor (or detector). Photons released by the emitter 802 will follow many different paths to each detector 804. For simplicity and clarity, the path that results from the optical power-weighted average of all the possible paths is described simply as the light path in some embodiments. In some alternative embodiments, "light path" refers to the path along which most of the photons travel. In yet other embodiments, "light path" refers to an approximated vector having an origin at a center of a light source and terminating anywhere in the surface area of a detector 804, and representing an approximate path of light from the emitting source 802 to the detector 804.

As a light path represents an approximate path of light from a given emitter source 802 to a given detector 804, for example, if there are multiple emitters 802 and multiple detectors 804, then a distinct light path exists between each of the multiple sources and each of the multiple detectors. Consistent with the embodiments described herein, PPG signals associated with any of the aforementioned light paths may be selectively obtained and utilized for estimating HR and/or other physiological metrics. For example, the PPG signals corresponding to any of multiple paths may be compared using a quality/confidence metric such as a signal-to-noise ratio ("SNR"), and the PPG signal having the highest quality can be selected to be used for estimating the HR and/or other physiological data.

Figure 9:
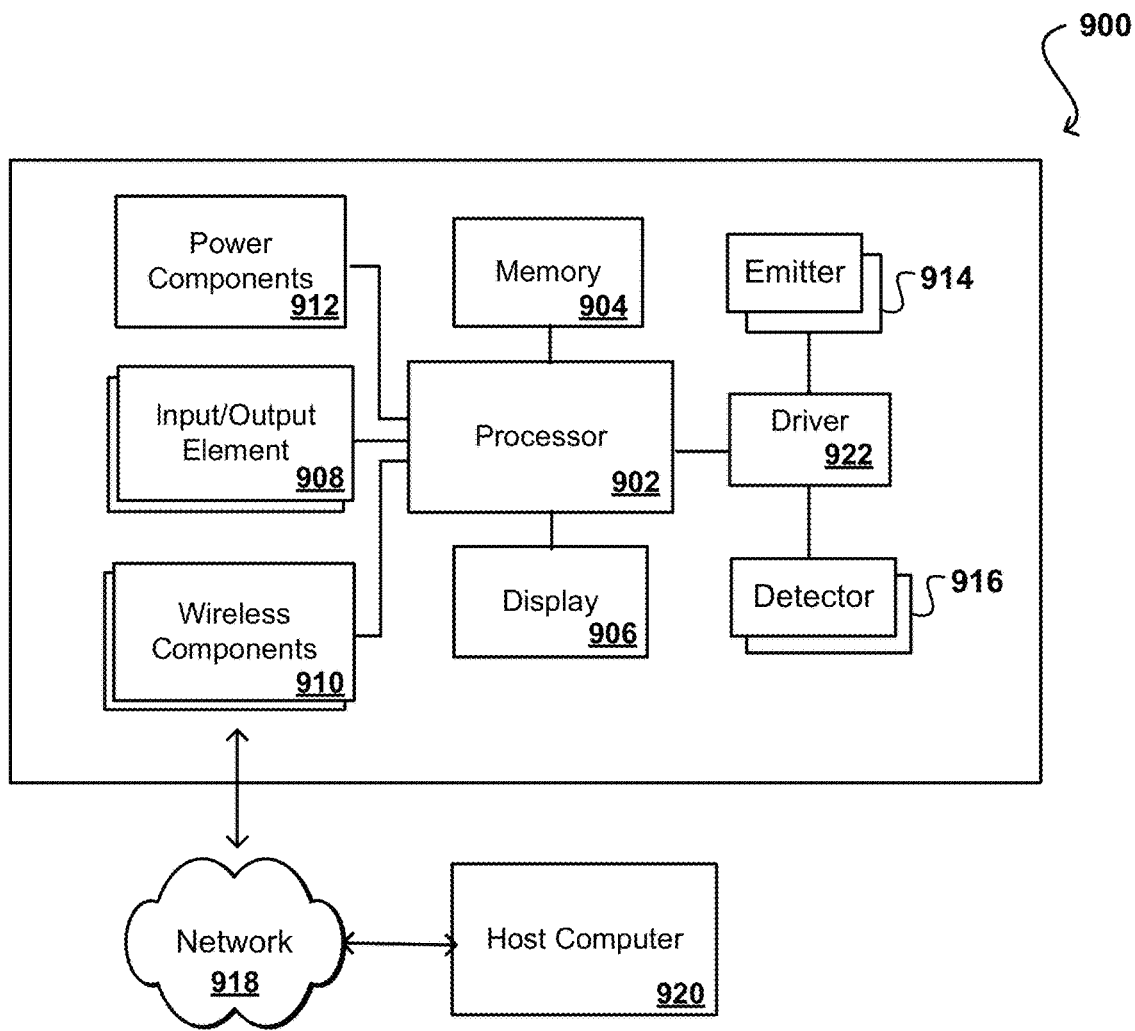
FIG. 9 illustrates components of an example network-connected monitoring device that can be utilized in accordance with various embodiments.

FIG. 9 illustrates components of an example computing device 900 that can be utilized in accordance with various embodiments. In this example, a monitoring or tracking device includes at least one processor 902, such as a central processing unit ("CPU") or graphics processing unit ("GPU") for executing instructions that can be stored in a memory device 904, such as may include flash memory or DRAM, among other such options. As would be apparent to one of ordinary skill in the art, the device can include many types of memory, data storage, or computer-readable media, such as data storage for program instructions for execution by a processor. The same or separate storage can be used for images or data; a removable memory can be available for sharing information with other devices, and any number of communication approaches can be available for sharing with other devices. The device typically will include some type of display 906, such as a touch screen, organic light emitting diode ("OLED"), or liquid crystal display ("LCD"), although devices might convey information via other means, such as through audio speakers or projectors.

A monitoring device or similar tracking device will include at least one motion detection sensor, which, as illustrated, can include at least one I/O element 908. That type of sensor can determine and/or detect orientation and/or movement of the device. Such an element can include, for example, an accelerometer, inertial sensor, altimeter, or gyroscope operable to detect movement (e.g., rotational movement, angular displacement, tilt, position, orientation, or motion along a non-linear path) of the device. An orientation-determining element can also include an electronic or digital compass, which can indicate a direction (e.g., north or south) in which the device is determined to be pointing (e.g., with respect to a primary axis or other such aspect). A device may also include an I/O element 908 for determining a location of the device (or the user of the device). Such a positioning element can include or comprise a Global Positioning System ("GPS") or similar location-determining element(s) operable to determine relative coordinates for a position of the device. Positioning elements may include wireless access points, base stations, etc., that may either broadcast location information or enable triangulation of signals to determine the location of the device. Other positioning elements may include QR codes, barcodes, RFID tags, NFC tags, etc., that enable the device to detect and receive location information or identifiers allowing the device to obtain the location information (e.g., by mapping the identifiers to a corresponding location). Various embodiments can include one or more such elements in any appropriate combination. The I/O elements 908 may also include one or more biometric sensors, optical sensors, barometric sensors (e.g., altimeter), and the like.

As mentioned above, some embodiments use the element(s) to track the location and/or motion of a user. Upon determining an initial position of a device (e.g., using GPS), the device may track of the location of the device by using the element(s), or in some instances, by using the orientation determining element(s) as mentioned above, or a combination thereof. As should be understood, the algorithms or mechanisms used for determining a position and/or orientation can depend at least in part upon the selection of elements available to the device. The example device also includes one or more wireless components 910 operable to communicate with one or more electronic devices within a communication range of the particular wireless channel. The wireless channel can be any appropriate channel used to enable devices to communicate wirelessly, such as Bluetooth, cellular, NFC, or Wi-Fi channels. It should be understood that the device can have one or more conventional wired communications connections as known in the art. The device also includes one or more power components 912, such as may include a battery operable for recharging through conventional plug-in approaches or through other approaches such as capacitive charging through proximity with a power mat or other such device. In some embodiments, the device can include at least one additional input/output device 908 able to receive conventional input from a user. This conventional input can include, for example, a push button, touch pad, touch screen, wheel, joystick, keyboard, mouse, keypad, or any other such device or element whereby a user can input a command to the device. These I/O devices 908 could even be connected by a wireless infrared or Bluetooth or other link as well in some embodiments. Some devices also can include a microphone or other audio capture element that accepts voice or other audio commands. For example, a device might not include any buttons at all, but might be controlled only through a combination of visual and audio commands, such that a user can control the device without having to be in contact with the device.

As mentioned, many embodiments will include at least some combination of one or more emitters 914 and one or more detectors 916 for measuring data for one or more metrics of a human body, such as for a person wearing the tracker device. In some embodiments, this may involve at least one imaging element, such as one or more cameras that are able to capture images of the surrounding environment and that are able to image a user, people, or objects in the vicinity of the device. The image capture element can include any appropriate technology, such as a CCD image capture element having a sufficient resolution, focal range, and viewable area to capture an image of the user when the user is operating the device. Methods for capturing images using a camera element with a computing device are well known in the art and will not be discussed herein in detail. It should be understood that image capture can be performed using a single image, multiple images, periodic imaging, continuous image capturing, image streaming, etc. Further, a device can include the ability to start and/or stop image capture, such as when receiving a command from a user, application, or other device.

In line with the optical-oriented discussions herein, the example device in the FIG. 9 system includes emitters 914 and detectors 916 capable of being used for obtaining optical photoplethysmogram ("PPG") measurements. Some PPG technologies rely on detecting light at a single spatial location, or adding signals taken from two or more spatial locations. Both of these approaches result in a single spatial measurement from which the HR estimate (or other physiological data) can be determined. In some embodiments, a PPG device employs a single light source 914 coupled to a single detector 916 (i.e., a single light path). Alternatively, a PPG device may employ multiple light sources 914 coupled to a single detector or multiple detectors 916 (i.e., two or more light paths). In other embodiments, a PPG device employs multiple detectors 916 coupled to a single light source or multiple light sources 914 (i.e., two or more light paths). In some cases, the light source(s) 914 may be configured to emit one or more of green, red, and/or infrared light. For example, a PPG device may employ a single light source 914 and two or more light detectors 916 each configured to detect a specific wavelength or wavelength range. In some cases, each detector 916 is configured to detect a different wavelength or wavelength range from one another. In other cases, two or more detectors 916 are configured to detect the same wavelength or wavelength range. In yet another case, one or more detectors 916 are configured to detect a specific wavelength or wavelength range different from one or more other detectors). In embodiments employing multiple light paths, the PPG device may determine an average of the signals resulting from the multiple light paths before determining an HR estimate or other physiological metrics. Such a PPG device may not be able to resolve individual light paths or separately utilize the individual signals resulting from the multiple light paths.

In some embodiments a user wearing a monitoring device with PPG functionality might perform an activity involving motion (or contorting of the wrist, for example, for a wrist-worn PPG device, thereby affecting the dynamics of the blood flow within the wrist). In such instances the accuracy of the HR estimate provided by the PPG device may be reduced or compromised. The light intensity received by the light detectors 916 may be modulated by these movements typically at an order of magnitude or greater than the desired cardiac signal. Therefore, a preprocessing step where the signal effect of these movements is removed can be utilized to improve HR estimation accuracy during motion. In addition to the deleterious effects of motion, another cause of reduced signal quality in PPG devices may be the characteristics of the local area being sensed. For instance, signal quality can vary dramatically if a wrist-worn PPG sensor is moved only a few millimeters up or down the wrist. In addition, during motion, certain portions of the wrist-worn PPG devices may be subject to more motion depending on their location, position, and/or orientation, and PPG sensors placed on such portions may therefore result in greater degradation of the PPG signal due to motion.

Various embodiments enable a PPG device to utilize signals based on two or more independently addressable source-detector combinations such that the signal quality of the PPG device is improved, especially during activities involving motion. In some embodiments, PPG signals can be acquired via multiple light paths involving one or more sources and one or more detectors placed at different spatial locations. These multiple PPG signals can then be processed to isolate the cardiac component (e.g., by removing the motion component) from the PPG signals. For example, the motion component may be removed based on inputs from the accelerometer, unsupervised learning and/or previously done supervised learning. Additionally, or alternatively, the PPG signals corresponding to these multiple light paths are compared using a quality metric such that the highest-quality PPG signal can be selected for estimating HR or other physiological metrics, as well as sleep time or other potential aspects.

In order to utilize two or more source-detector pairs for motion signal rejection, a PPG device in accordance with various embodiments can use a computer program to identify the motion component of a given signal and remove the motion component from the composite signal, leaving only the cardiac signal as a remainder. In some implementations, the temporal phase of the cardiac waveform is assumed to stay constant between different light paths, while the phase of the motion signal is expected to vary between light paths, due to how the PPG sensor interacts with the skin surface during activities involving motion (e.g., pressure at the PPG/skin interface may vary depending on the spatial location of the light source and the light detector of the light path). Using this concept, PPG devices can fit mathematical models to the spatial light path signals to identify the cardiac and motion components. First, PPG signals are extracted by each source-detector combination. For example, two light sources 914 and two light detectors 916 would result in four source-detector combinations. A mathematical model can then be fit to the different spatial points, from which characteristic signals are extracted related to the cardiac and motion components of the PPG signals. PPG devices may also implement other techniques including, but not limited to, independent component analysis ("ICA") and other forms of blind source separation.

Although some embodiments are described with reference to HR or cardiac components of PPG signals, the techniques described herein may be extended to other types of physiological data described herein, such as may relate to $SpO_2$ or other types of signals that can be extracted from the PPG signals to determine physiological data or metrics. For example, in some embodiments, a method for determining an $SpO_2$ value comprises receiving a first set of one or more PPG signals from one or more PPG sensors 916, which may include analog signals or digital data sampled from analog components and stored in computer memory. The first set of PPG signals may correspond to red and/or infrared light previously emitted by one or more emitters 914 after the emitted light has interacted with the user's skin, when the monitoring device is worn by the user. A first set of PPG signals may include a noise component. The method for determining the $SpO_2$ value may further comprise receiving a second set of one or more PPG signals from the one or more PPG sensors or detectors, which may include analog signals or digital data sampled from analog components and stored in computer memory. For example, the second set of PPG signals may be obtained from different ranges of wavelengths emitted from the light source 914 than the first set of PPG signals. The second set of PPG signals may be obtained from one or more green light sources 914. In some cases, the second set of PPG signals is obtained from a system within the device used for tracking a user's heart rate. In other cases, the second set of PPG signals is received from a system separate from HR detection. The method for determining the $SpO_2$ value may further comprise filtering the first set of PPG signals based on a feature of the second set of PPG signals, to generate a filtered set of PPG signals. Various filtering techniques may be used to remove noise or other features from the first set of PPG signals based on a feature of the second set of PPG signals. As but one example, HR may be the feature of the second set of PPG signals. In the case of HR, the device may create a filter based at least in part upon the detected frequency of the HR signal. Examples of filters include a low-pass filter, a high-pass filter, and a narrow-band filter that excludes frequencies that are inconsistent with the frequency of the HR signal. The method for determining the $SpO_2$ value may further comprise using one range of wavelengths to better measure an underlying signal on which the wavelengths of the first set of PPG signals operates. Based on this underlying signal (or features derived therefrom), the device can improve the first set of PPG signals based on filtering noise from the first set of PPG signals. Further, the filtered set of PPG signals can be used to create and store a $SpO_2$ value. As an example, the filtered set of PPG signals may have a reduced or eliminated noise component and therefore may serve as a more accurate basis for creating and storing the $SpO_2$ value.

In some embodiments, an intermediate HR estimation can be performed based on PPG signals from two or more light paths. For each of the acquired PPG signals, the PPG device may determine an estimate of the HR in beats-per-minute ("BPM") and compute a confidence metric associated with the PPG signal, indicative of the signal quality for the particular light path associated with the PPG signal. It may also be possible to compute a confidence metric without an intermediate HR estimation, for example via characteristics (e.g., statistics) of the PPG signal or filtered versions of the PPG signal. In some embodiments, each confidence metric corresponds to a single PPG signal. In other cases, each confidence metric corresponds to multiple PPG signals. By way of specific example, a confidence metric may be computed for each way of combining the PPG signals (e.g., signals A+B, signals A+C, signals B+C, and signals A+B+C), as well as for various combinations of PPG signals (e.g., selecting at least two of signals A, B, and C). In other cases, one confidence metric corresponds to a single PPG signal and another confidence metric corresponds to a combination of multiple PPG signals. The PPG device can select an HR estimate from the multiple HR estimates corresponding to the multiple light paths (e.g., by selecting the HR estimate of the PPG signal having the highest confidence metric). Alternatively, the PPG device may assign different weight values to the multiple HR estimates based on the confidence metric values associated with the individual and/or multiple PPG signals and compute a final HR estimate based on the weight values. As with other aspects of the present disclosure, the confidence values and/or the weight values may be updated or optimized using machine learning. The PPG device may implement hysteresis logic which prevents jumping between light paths in a short time window if the confidence metric values corresponding to the two light paths are within a threshold value. The PPG device may also implement logic configured to bias the selection of HR estimates based on user data, activity data, movement data, or other data accessible by the PPG device. The PPG device may apply a smoothing filter on the HR estimates to, for example, improve accuracy and provide a better user experience.

One advantage of such an approach lies in the fact that the spatial information associated with the light sources 914 and/or light detectors 916 can be used by different algorithms to improve HR or other physiological metric estimation accuracy of the PPG sensing device, especially when the user of the device is exercising or performing activities involving motion. Existing implementations typically rely on algorithms to improve the HR or other physiological metric estimation performance, but do not have the benefit of the extra sensor data generated based on multiple light paths.

Referring to FIG. 9, an example monitoring device may comprise one or more processors 902 coupled to memory 904, a display 906, a bus, one or more input/output (I/O) elements 908, and wireless networking components 910, among other such options. A display 906 and/or I/O devices 908 may be omitted in certain embodiments. If included, a display 906 may provide an interface for displaying data, such as HR, blood oxygen saturation ($SpO_2$) levels, and other metrics of the user. For example, the processor 902 may compute values for the physiological metrics monitored by the device based on one or more PPG signals generated by detectors 916 of light. In an embodiment, the PPG device is a wristband, and the display is configured such that the display 906 faces away from the outside of a user's wrist when the user wears the PPG device. In other embodiments, the display 906 may be omitted and data detected by the PPG device may be transmitted using the wireless networking interface via near-field communication ("NFC"), Bluetooth, Wi-Fi, or other suitable wireless communication protocols over at least one network 918 to a host computer 920 for analysis, display, reporting, or other such use.

The memory 904 may comprise RAM, ROM, FLASH memory, or other non-transitory digital data storage, and may include a control program comprising sequences of instructions which, when loaded from the memory and executed using the processor 902, cause the processor 902 to perform functions described herein. The emitters 914 and detectors 916 may be coupled to a bus directly or indirectly using driver circuitry 922 by which the processor 902 may drive the light emitters 914 and obtain signals from the light detectors 916. The host computer 920 may communicate with the wireless networking components 910 via one or more networks 918, which may include one or more local area networks, wide area networks, and/or the internet using any of terrestrial or satellite links. In some embodiments, the host computer 920 executes control programs and/or application programs configured to perform some of the functions described herein.

In some embodiments, each emitter 914 can be individually controlled, or each light detector 916 can be individually read out when multiple detectors 916 are used, and in such embodiments, PPG sensor data along several different light paths can be collected. The control program can utilize the collected data to provide a more accurate estimation or HR and/or other physiological metrics. In related aspects, the processor 902 and other component(s) of the PPG monitoring device may be implemented as a System-on-Chip ("SoC") that may include one or more CPU cores that use one or more reduced instruction set computing ("RISC") instruction sets, and/or other software and hardware to support the monitoring device.

In various embodiments, the emitters (or light sources) 914 comprise electronic semiconductor light sources, such as LEDs, or produce light using any of filaments, phosphors, or laser. In some implementations, each of the light sources 914 emits light having the same center wavelength or within the same wavelength range. In other cases, at least one light source 914 may emit light having a center wavelength that is different from another one of the light sources 914. The center wavelengths of the light emitted by the light sources 914 may be in the range of 495 nm to 570 nm. For example, a particular green light source 914 may emit light with a center wavelength of 528 nm. In other embodiments, one or more of the light sources 914 may emit red light (e.g., 660 nm center wavelength) or IR light (e.g., 940 nm center wavelength). In some embodiments, one or more of the light sources 914 may emit light with peak wavelengths typically in the range of 650 nm to 940 nm. More particularly, a red light source 914 may emit light with a peak wavelength of 660 nm, and one or more infrared light sources 914 may emit light with peak wavelengths in the range of 750 nm to 1700 nm. By way of example and not any sort of limitation, a particular infrared light source 914 may emit light with a peak wavelength of 730 nm, 760 nm, 850 nm, 870 nm, or 940 nm. In some cases, commercial light sources such as LEDs may provide output at about 20 nm intervals with a center wavelength tolerance of +/−10 nm from the manufacturer's specified wavelength and thus one possible range of useful peak wavelengths for the light sources is 650 nm to 950 nm. The green light sources 914 may be configured to emit light with wavelengths in the range of 495 nm to 570 nm. For example, a particular green light source 914 may emit light with a wavelength of 528 nm. The green light sources 914 may be as equally spaced from light detectors 916 as the pairs of red and infrared light sources 914. If, say, the distance between light detectors 916 and a center of a first red light source 914 is 2 mm, the distance between light detectors 916 and a green light source 914 may also be 2 mm (e.g., equidistant). In some other cases, the distance between the light detectors 916 and one or more light sources 914 is not equidistant. Further, in some embodiments, one or more of the light sources 914 may comprise a single LED package that emits multiple wavelengths, such as green, red and infrared wavelengths, at the same or substantially the same (e.g., less than 1 mm difference) location with respect to multiple detectors 916. Such LEDs may include multiple semiconductor elements co-located using a single die in a single package.

The spacing of the light sources 914 may be measured from the side of the light source 914 or the center of the light source 914. For example, the light sources 914 may be configured such that the center of each light source 914 is at a first distance from the edge of the closest one of the light detectors 916. In an illustrative embodiment, the first distance may be 2 mm. In some implementations, each light source 914 is located at a second distance from the closest one of the light sources 914, and each light detector 916 is located at a third distance from the closest one of the light detectors 916. In some embodiments, the second and third distances are identical to the first distance. In other embodiments, each of the second and third distances is different from the first distance. The second distance may be identical to or different from the third distance. The particular magnitude of the spacing may depend on a number of factors and this disclosure does not limit the embodiments to any particular spacing. For example, spacing in a range of 1 mm (or less) to 10 mm would be workable in various embodiments.

In some embodiments, independent control of all light sources 914 is provided. In other embodiments, several light sources 914 are controlled together as a gang or bank. A benefit of independent control of each light source 914, or independent readout from each of multiple detectors 916 (e.g., obtaining independent signals based on the same or different light wavelengths from each of multiple detectors), is that a multiple light path approach may be used to improve the estimation of HR and/or other physiological metrics, as discussed herein.

Light detectors 916 may comprise one or more sensors that are adapted to detect wavelengths of light emitted from the light sources 914. A particular light source 914 combined with a particular detector may comprise a sensor such as a PPG sensor. A first PPG sensor and a second PPG sensor can share components, such as the same light sources 914 and/or detectors 916, or have different components and thus the term "PPG sensor," in addition to having its ordinary meaning, may refer to any of such arrangements although actual embodiments may use multiple components in implementing a PPG sensor. The term "PPG device," in addition to having its ordinary meaning, may refer to any device including a PPG sensor. A light detector 916, in an embodiment, may comprise one or more detectors 916 for detecting each different wavelength of light that is used by the light sources 914. For example, a first detector 916 may be configured to detect light with a wavelength of 560 nm, a second detector 916 may be configured to detect light with a wavelength of 940 nm, and a third detector 916 may be configured to detect light with a wavelength of 528 nm. Examples include photodiodes fabricated from semiconductor materials and having optical filters that admit only light of a particular wavelength or range of wavelengths. The light detectors 916 may comprise any of a photodiode, phototransistor, charge-coupled device ("CCD"), thermopile detector, microbolometer, or complementary metal-oxide-semiconductor ("CMOS") sensor. The light detectors 916 may comprise multiple detector elements, as further described herein. One or more of the detectors 916 may comprise a bandpass filter circuit.

In other embodiments, a detector 916 may comprise one or more detectors 916 configured to detect multiple wavelengths of light. For example, a single detector 916 may be configured to tune to different frequencies based on data received from an electrical digital microprocessor coupled to detectors. In another way, the single detector 916 may include multiple active areas where each active area is sensitive to a given range of wavelengths. A single detector 916 may be configured to detect light with wavelengths in the red and IR frequencies, and a second detector 916 is configured to detect light with wavelengths in the green frequencies. Further, each of the light sources 914 may use any of one or more different wavelengths of light as previously described.

In an embodiment, light detectors 916 can be mounted in a housing with one or more filters that are configured to filter out wavelengths of light other than wavelengths emitted by light sources 914. For example, a portion of the housing may be covered with a filter which removes ambient light other than light in wavelengths emitted by light sources 914. Signals from light sources 914 may be received at the light detectors 916 through an ambient light filter that filters out an ambient light source generating ambient light with a wavelength differing from the wavelength that is detected by the detector 916. Although LEDs and photodiodes are used as examples of the light sources 914 and the light detectors 916, respectively, the techniques described herein may be extended to other types of light sources, such as edge emitting lasers, surface emitting lasers, and LED-pumped phosphors that generate broadband light. And the techniques may be extended to other combinations of light sources and detectors as well. For example, the PPG device may include: (i) single or multiple LEDs and a multi-element photodetector (e.g., a camera sensor); (ii) an LED array and single or multiple photodiodes; (iii) a broadband LED-pumped phosphor and detector array with wavelength selective filters on each detector; (iv) a spatial light modulator ("SLM") (e.g., a digital micromirror device ("DMD"); or (v) a liquid crystal on silicon ("LCoS") device) and single or multiple LEDs, other combinations thereof, or other configurations of light sources and detectors).

While certain flow discussions and diagrams are presented herein to illustrate various methods that may be performed by example embodiments, such merely illustrates example algorithms that may be programmed, using any suitable programming environment or language, to create machine code capable of execution by a CPU or microcontroller of the PPG device. In other words, the flow diagrams, together with the written description in this document, are disclosures of algorithms for aspects of the claimed subject matter, presented at the same level of detail that is normally used for communication of this subject matter among skilled persons in the art to which the disclosure pertains. Various embodiments may be coded using assembly, C, Objective-C, C++, Java, or other human-readable languages and then compiled, assembled, or otherwise transformed into machine code which can be loaded into ROM, EPROM, or other recordable memory of the monitoring device apparatus that is coupled to the CPU or microcontroller and then then executed by the CPU or microcontroller.

In an embodiment, PPG signals obtained from multiple light paths may be processed to filter or reject signal components associated with motion of the user, using a computer application or program to identify the motion component of the signal and remove the identified motion component from the composite signal, leaving the cardiac component as a remainder or final signal. PPG signals might be collected in variety of activities during day or at night, such as may relate to periods of walking, exercise, or sleep. Other on-device sensors including an accelerometer, gyroscope, or altimeter may be used to categorize or detect the activity, or human posture as a basis to develop the appropriate filters. These filters or signal processing methods might be used for targeted reduction of variability in the PPG data with multiple light paths. As an example and not a limitation, the accelerometer data can be used to develop signal processing methods to filter the PPG data and look into a certain posture, removing other body orientations. This can help reduce the noise in the PPG data and get a better assessment of the corresponding physiological variables for the corresponding light paths.

In various embodiments, approaches discussed herein may be performed by one or more of: firmware operating on a monitoring device or a secondary device, such as a mobile device paired to the monitoring device, a server, host computer, and the like. For example, the monitoring device may execute operations relating to generating signals that are uploaded or otherwise communicated to a server that performs operations for removing the motion components and creating a final estimate value for HR, $SpO_2$, and/or other physiological data metrics. Alternatively, the monitoring device may execute operations pertinent to generating the monitoring signals and removing the motion components to produce a final estimate value for HR, $SpO_2$, and/or other physiological metrics local to the monitoring device. In this case, the final estimate may be uploaded or otherwise communicated to a server such as a host computer that performs other operations using the value.

An example monitoring or tracker device, such as one having components depicted in FIG. 9, can collect one or more types of physiological and/or environmental data from one or more sensor(s) and/or external devices and communicate or relay such information to other devices (e.g., a host computer or another server), thus permitting the collected data to be viewed, for example, using a Web browser or network-based application. For example, while being worn by the user, a monitoring device may perform biometric tracking via calculating and storing the user's step count using one or more sensor(s). The monitoring device may transmit data representative of the user's step count to an account on a Web service (e.g., www.fitbit.com), computer, mobile phone, and/or health station where the data may be stored, processed, and/or visualized by the user. As noted, the monitoring device may measure or calculate many other physiological data metrics in addition to, or in place of, the user's step count. Again, such physiological data may include, but are not limited to: energy expenditure (e.g., calories burned); floors climbed and/or descended; HR; heartbeat waveform; HR variability; HR recovery; respiration; $SpO_2$; blood volume; blood glucose; skin moisture; skin pigmentation level; location and/or heading (e.g., via a GPS, global navigation satellite system (GLONASS), or a similar system); elevation; ambulatory speed and/or distance traveled; swimming lap count; swimming stroke type and count detected; bicycle distance and/or speed; skin conduction; skin and/or body temperature; muscle state measured via electromyography; brain activity as measured by electroencephalography; weight; body fat; caloric intake; nutritional intake from food; medication intake; sleep periods (e.g., clock time, sleep phases, sleep quality, and/or duration); pH levels; hydration levels; respiration rate; and/or other metrics.

An exemplary device for monitoring or tracking may also measure or calculate metrics related to the environment around the user (e.g., with one or more environmental sensor(s)), such as, for example, barometric pressure, weather conditions (e.g., temperature, humidity, pollen count, air quality, rain/snow conditions, wind speed), light exposure (e.g., ambient light, ultra-violet (UV) light exposure, time, and/or duration spent in darkness), noise exposure, radiation exposure, and/or magnetic field. Furthermore, a monitoring device (and/or the host computer and/or another server) may collect data from one or more sensors of the device and may calculate metrics derived from such data. For example, a monitoring device may calculate the user's stress or relaxation levels based on a combination of HR variability, skin conduction, noise pollution, and/or sleep quality. In yet another example, a monitoring device may determine the efficacy of a medical intervention, such as based on a combination of data relating to medication intake, sleep, and/or activity. Again, examples herein are provided for illustration only and are not intended to be limiting or exhaustive.

An example monitoring device may also include a computer-readable storage media reader, a communications device (e.g., a modem, a network card (wireless or wired), and/or an infrared communication device), and working memory 904 as described above. The computer-readable storage media reader can be connected with, or configured to receive, a computer-readable storage medium representing remote, local, fixed and/or removable storage devices as well as storage media for temporarily and/or more permanently containing, storing, transmitting, and retrieving computer-readable information. A monitoring system and various devices also typically will include a number of software applications, modules, services, or other elements located within at least one working memory device 904, including an operating system and application programs such as a client application or Web browser. It should be appreciated that alternate embodiments may have numerous variations from that described above. For example, customized hardware might also be used and/or particular elements might be implemented in hardware, software (including portable software, such as applets), or both. Further, connection to other computing devices, such as network input/output devices, may be employed.

Storage media and other non-transitory computer readable media for containing code, or portions of code, can include any appropriate media known or used in the art, including, but not limited to, volatile and non-volatile, removable, and non-removable media implemented in any method or technology for storage of information, such as computer readable instructions, data structures, program modules or other data, including RAM, ROM, EEPROM, flash memory or other memory technology, CD-ROM, digital versatile disk ("DVD") or other optical storage, magnetic cassettes, magnetic tape, magnetic disk storage or other magnetic storage devices, or any other medium which can be used to store the desired information and which can be accessed by a system device.

Based on the disclosure and teachings provided herein, a person of ordinary skill in the art will appreciate other ways and/or methods to implement the various embodiments. The specification and drawings are, accordingly, to be regarded in an illustrative, rather than a restrictive, sense. It will, however, be evident that various modifications and changes may be made thereunto without departing from the broader spirit and scope of the invention as set forth in the claims.

What is claimed is:

1. A computer-implemented method, comprising:
   obtaining sleep-related data for a user collected over multiple sleep periods, wherein at least a subset of the sleep-related data is obtained from a wearable monitoring device worn by the user;
   determining, from the sleep-related data, user values for a plurality of pre-defined sleep metrics;
   comparing the user values against sleep metric values for the plurality of pre-defined sleep metrics for each of a plurality of different and pre-defined sleeper types that correspond to a plurality of different sleep patterns to identify a sleeper type that most closely represents the sleep of the user, wherein each sleeper type of the plurality of different and pre-defined sleeper types is determined based at least in part on clustering of an initial set of sleep features to generate a set of clusters corresponding to the plurality of different and pre-defined sleeper types;
   causing information pertaining to the identified sleeper type for the user to be displayed, the information comprising a graphical object representative of the identified sleeper type, the information further comprising a graphical comparison of the user values for the plurality of pre-defined sleep metrics to sleep metric values for the plurality of pre-defined sleep metrics for an average user of the identified sleeper type of the user wearing the wearable monitoring device;
   causing a graphical comparison of the user values for the plurality of pre-defined sleep metrics to sleep metric values for the plurality of pre-defined sleep metrics for an average user of at least one other sleeper type of the plurality of pre-defined sleeper types to be displayed, the at least one other sleeper type being different than the identified sleeper type of the user wearing the monitoring device; and causing an electronic device, associated with the user, to make at least one adjustment based at least in part upon the identified sleeper type for the user.

2. The computer-implemented method of claim 1, further comprising:
generating at least one recommendation to present to the user to help improve the sleep of the user, the at least one recommendation determined based at least in part upon the user values for the plurality of pre-defined sleep metrics and the identified sleeper type for the user.

3. The computer-implemented method of claim 2, further comprising:
determining a current state of at least one of the user or an environment of the user, wherein the at least one recommendation or the at least one adjustment is determined based further upon the current state.

4. The computer-implemented method of claim 1, wherein at least a subset of the sleep-related data is further obtained from a computing device associated with the user or a sensory device located in an environment surrounding the user.

5. The computer-implemented method of claim 1, further comprising:
collecting sleep-related data for a population of users;
determining the initial set of sleep features from the sleep-related data; and
performing clustering of the initial set of sleep features to generate a set of clusters corresponding to the plurality of different and pre-defined sleeper types.

6. The computer-implemented method of claim 5, further comprising:
identifying the sleeper type for the user using one or more distance heuristics to compare the user values against the respective sleep metric values of the set of clusters.

7. The computer-implemented method of claim 1, wherein the graphical object is capable of being animated to convey a subset of the information to the user.

8. The computer-implemented method of claim 7, wherein the graphical object is a sleep animal.

9. The computer-implemented method of claim 1, wherein the at least one adjustment to be made by the electronic device includes at least one of a change in display, volume, brightness, mode, operational state, power level, communication, configuration, or operation, and wherein the adjustment is intended to assist a user in achieving a desired sleep goal.

10. The computer-implemented method of claim 1, wherein the multiple sleep periods correspond to multiple days in which the user had an opportunity to sleep.

11. The computer-implemented method of claim 1, wherein causing a graphical comparison of the user values for the plurality of pre-defined sleep metrics to sleep metric values for the plurality of pre-defined sleep metrics for an average user of at least one other sleeper type of the plurality of sleeper types to be displayed comprises causing a graphical comparison of the user values for the plurality of pre-defined sleep metrics to sleep metric values for the plurality of pre-defined sleep metrics for an average user of every other sleeper type of the plurality of pre-defined sleeper types to be displayed.

12. The computer-implemented method of claim 1, further comprising:
generating a sleeper bio for the user based, at least in part, on the identified sleeper type.

13. A monitoring device, comprising:
a display device;
a non-invasive measurement system;
at least one processor; and
memory including instructions that, when executed by the at least one processor, cause the monitoring device to:
obtain, using the non-invasive measurement system, sleep-related data for a user over multiple sleep periods;
cause user values for a plurality of pre-defined sleep metrics to be determined from at least the sleep-related data;
cause the user values to be compared against sleep metric values for the plurality of pre-defined sleep metrics for each of a plurality of different and pre-defined sleeper types that correspond to a plurality of different sleep patterns to identify a sleeper type that most closely represents the sleep of the user, wherein each type of the plurality of different and pre-defined sleeper types is determined based at least in part on clustering of an initial set of sleep features to generate a set of clusters corresponding to the plurality of different and pre-defined sleeper types;
cause information pertaining to the identified sleeper type for the user to be displayed on the display device, the information comprising a graphical object representative of the identified sleeper type;
cause a graphical comparison of the user values for the plurality of pre-defined sleep metrics to sleep metric values for the plurality of pre-defined sleep metrics for an average user of at least one other sleeper type of the plurality of pre-defined sleeper types to be displayed on the display device, the at least one other sleeper type being different than the identified sleeper type for the user; and
trigger at least one automated change based at least in part upon the identified sleeper type.

14. The monitoring device of claim 13, wherein the automated change is to at least one of the monitoring device or an external electronic device, and wherein the automated change is intended to help improve the sleep of the user.

15. The monitoring device of claim 13, wherein the instructions when executed further cause the monitoring device to:
cause at least one recommendation for improving the sleep of the user to be displayed on the display device, the recommendation determined based at least in part upon the identified sleeper type.

16. The monitoring device of claim 13, wherein the user values for the plurality of pre-defined sleep metrics are further determined based upon sleep-related data obtained from one or more external data sources.

17. A sleep improvement system, comprising:
one or more processors; and
memory including instructions that, when executed by the one or more processors, causes the sleep improvement system to:
obtain, from one or more electronic devices, wherein the one or more electronic devices include at least one wearable monitoring device, sleep-related data for a user collected over multiple sleep periods;
determine, from the sleep-related data, user values for a plurality of pre-defined sleep metrics;
compare the user values against sleep metric values for the plurality of pre-defined sleep metrics for each of a plurality of different and pre-defined sleeper types that correspond to a plurality of different sleep patterns to identify a sleeper type that most closely represents the sleep of the user, wherein each sleeper type of the plurality of different and pre-defined sleeper types is determined based at least in part on clustering of an initial set of sleep features to generate a set of clusters corresponding to the plurality of different and pre-defined sleeper types;

cause a graphical comparison of the user values for the plurality of pre-defined sleep metrics to sleep metric values for the plurality of pre-defined sleep metrics for an average user of at least one other sleeper type of the plurality of pre-defined sleeper types to be displayed on a display device, the at least one other sleeper type being different than the identified sleeper type of the user wearing the monitoring device; and cause an electronic device, of the one or more electronic devices, to make at least one adjustment based at least in part upon the identified sleeper type for the user.

18. The sleep improvement system of claim 17, wherein the at least one adjustment includes causing a graphical comparison of the user values for the plurality of pre-defined sleep metrics to sleep metric values for the plurality of pre-defined sleep metrics for an average user of the identified sleeper type of the user wearing the monitoring device.

19. The sleep improvement system of claim 17, wherein the one or more electronic devices include at least one of a sensory device, a user computing device, or a network-connected smart device capable of providing at least a subset of the sleep-related data.

20. The sleep improvement system of claim 17, wherein the instructions when executed further cause the sleep improvement system to:

generate at least one recommendation to present to the user to help improve the sleep of the user, the at least one recommendation determined based at least in part upon the user values for the plurality of pre-defined sleep metrics and the identified sleeper type for the user.

* * * * *